US012090629B2

(12) United States Patent
Das et al.

(10) Patent No.: US 12,090,629 B2
(45) Date of Patent: Sep. 17, 2024

(54) ADAPTIVE ROBOTIC NURSING ASSISTANT

(71) Applicant: University of Louisville Research Foundation, Inc., Louisville, KY (US)

(72) Inventors: Sumit Kumar Das, Louisville, KY (US); Mohammad Nasser Saadatzi, Louisville, KY (US); Indika B. Wijayasinghe, Louisville, KY (US); Shamsudeen Olawale Abubakar, Louisville, KY (US); Christopher Kevin Robinson, Louisville, KY (US); Dan O. Popa, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 134 days.

(21) Appl. No.: 17/604,035

(22) PCT Filed: Apr. 16, 2020

(86) PCT No.: PCT/US2020/028472
§ 371 (c)(1),
(2) Date: Oct. 15, 2021

(87) PCT Pub. No.: WO2020/214787
PCT Pub. Date: Oct. 22, 2020

(65) Prior Publication Data
US 2022/0152837 A1 May 19, 2022

Related U.S. Application Data

(60) Provisional application No. 62/834,689, filed on Apr. 16, 2019.

(51) Int. Cl.
*B25J 11/00* (2006.01)
*A61G 12/00* (2006.01)
(Continued)

(52) U.S. Cl.
CPC ............ *B25J 11/009* (2013.01); *A61G 12/00* (2013.01); *A61H 3/04* (2013.01); *A61L 2/10* (2013.01);
(Continued)

(58) Field of Classification Search
CPC ...... B25J 11/009; B25J 13/065; B25J 13/085; A61G 12/00; A61G 2203/20;
(Continued)

(56) References Cited

U.S. PATENT DOCUMENTS

| 4,119,900 A | 10/1978 | Kremnitz | |
| 8,065,051 B2 * | 11/2011 | Chopcinski | G05B 19/106 701/1 |

(Continued)

FOREIGN PATENT DOCUMENTS

| AU | 2015218522 A1 * | 9/2015 | ............ B25J 11/009 |
| BR | 112013030509 B1 * | 11/2020 | ....... A61B 17/00234 |

(Continued)

OTHER PUBLICATIONS

International Search Report and Written Opinion corresponding to International Patent Application Serial No. PCT/US2020/028472 dated Jun. 22, 2020.

*Primary Examiner* — Atul Trivedi
(74) *Attorney, Agent, or Firm* — Jenkins, Taylor & Hunt, P.A.

(57) ABSTRACT

This specification describes an adaptive robotic nursing assistant for physical tasks and patient observation and feedback. In some examples, the adaptive robotic nursing assistant includes an omni-directional mobile platform; a footrest on the omni-directional mobile platform; a handlebar located above the footrest such that a user standing on the footrest can grasp the handlebar; a display above the handlebar and at least one user input device; a robot manipu- (Continued)

lator comprising a robotic arm and an end effector on the robotic arm; and a control system coupled to the omni-directional mobile platform, the control system comprising at least one processor and memory storing executable instructions for the at least one processor to control the omni-directional mobile platform.

18 Claims, 22 Drawing Sheets

(51) Int. Cl.
| | |
|---|---|
| A61H 3/04 | (2006.01) |
| A61L 2/10 | (2006.01) |
| A61L 2/18 | (2006.01) |
| B25J 5/00 | (2006.01) |
| B25J 13/06 | (2006.01) |
| B25J 13/08 | (2006.01) |
| B60B 19/00 | (2006.01) |
| B60K 1/02 | (2006.01) |
| B62D 51/02 | (2006.01) |
| B62D 51/04 | (2006.01) |
| G05D 1/00 | (2024.01) |

(52) U.S. Cl.
CPC ............... *A61L 2/18* (2013.01); *B25J 5/007* (2013.01); *B25J 13/065* (2013.01); *B25J 13/085* (2013.01); *B60K 1/02* (2013.01); *B62D 51/02* (2013.01); *G05D 1/021* (2013.01); *A61G 2203/20* (2013.01); *A61G 2203/22* (2013.01); *A61G 2203/32* (2013.01); *A61G 2203/72* (2013.01); *A61H 2003/043* (2013.01); *A61H 2201/1635* (2013.01); *A61H 2201/164* (2013.01); *A61H 2201/1659* (2013.01); *A61H 2201/5007* (2013.01); *A61H 2201/5043* (2013.01); *A61H 2201/5061* (2013.01); *A61H 2201/5092* (2013.01); *B60B 19/003* (2013.01); *B62D 51/04* (2013.01)

(58) Field of Classification Search
CPC ............ A61G 2203/22; A61G 2203/32; A61G 2203/72; A61H 3/04; A61H 2003/043; A61H 2201/1635; A61H 2201/164; A61H 2201/1659; A61H 2201/5007; A61H 2201/5043; A61H 2201/5061; A61H 2201/5092; A61L 2/10; A61L 2/18; B60K 1/02; B62D 51/02; B62D 51/04; G05D 1/021; G05D 2201/0206; B60B 19/003
USPC ......................................................... 701/25
See application file for complete search history.

(56) References Cited

U.S. PATENT DOCUMENTS

| | | | | |
|---|---|---|---|---|
| 8,380,350 | B2* | 2/2013 | Ozick | A47L 9/12 |
| | | | | 700/250 |
| 8,968,332 | B2* | 3/2015 | Farritor | A61B 5/05 |
| | | | | 606/1 |
| 10,016,900 | B1* | 7/2018 | Meyer | B25J 9/0084 |
| 10,136,947 | B2* | 11/2018 | Griffiths | B25J 5/007 |
| 10,687,915 | B2* | 6/2020 | Schlosser | F16M 13/022 |
| 2004/0251656 | A1* | 12/2004 | Patterson | A61G 7/1053 |
| | | | | 280/304.1 |
| 2007/0112458 | A1* | 5/2007 | Kondo | B66C 13/18 |
| | | | | 700/213 |
| 2011/0045194 | A1 | 2/2011 | Herre et al. | |
| 2011/0288573 | A1* | 11/2011 | Yates | A61B 50/36 |
| | | | | 227/175.1 |
| 2011/0290854 | A1* | 12/2011 | Timm | A61B 17/320068 |
| | | | | 227/178.1 |
| 2011/0295269 | A1* | 12/2011 | Swensgard | A61B 34/76 |
| | | | | 606/130 |
| 2012/0010749 | A1* | 1/2012 | van der Merwe | B25J 9/0006 |
| | | | | 700/264 |
| 2012/0328395 | A1* | 12/2012 | Jacobsen | B66F 9/18 |
| | | | | 414/1 |
| 2013/0325244 | A1* | 12/2013 | Wang | B25J 11/009 |
| | | | | 701/26 |
| 2014/0088761 | A1* | 3/2014 | Shamlian | G01B 11/026 |
| | | | | 700/253 |
| 2014/0200713 | A1* | 7/2014 | Allen | G05D 1/0272 |
| | | | | 901/1 |
| 2014/0243849 | A1* | 8/2014 | Saglam | A61B 34/75 |
| | | | | 606/130 |
| 2015/0359694 | A1* | 12/2015 | Suzuki | A61G 7/1046 |
| | | | | 901/2 |
| 2017/0348931 | A1 | 12/2017 | Yuzer et al. | |
| 2018/0014988 | A1 | 1/2018 | Diaz-Flores et al. | |
| 2019/0000559 | A1* | 1/2019 | Berman | A61B 5/6847 |
| 2019/0049977 | A1* | 2/2019 | Dean | G05D 1/0274 |
| 2019/0105776 | A1* | 4/2019 | Ho | A61B 34/70 |
| 2019/0107454 | A1* | 4/2019 | Lin | A61B 1/00149 |
| 2019/0248002 | A1* | 8/2019 | Deyle | B25J 19/023 |
| 2019/0248013 | A1* | 8/2019 | Deyle | B25J 13/006 |
| 2019/0248016 | A1* | 8/2019 | Deyle | B25J 13/006 |
| 2019/0327394 | A1* | 10/2019 | Ramirez Luna | H04N 23/51 |
| 2020/0008899 | A1* | 1/2020 | Tripathi | G02B 21/22 |
| 2020/0100845 | A1* | 4/2020 | Julian | A61G 13/04 |
| 2020/0405403 | A1* | 12/2020 | Shelton, IV | A61B 17/3421 |
| 2020/0405821 | A1* | 12/2020 | Harris | A61B 46/40 |
| 2022/0015773 | A1* | 1/2022 | Chappuis | A61B 34/30 |
| 2022/0126438 | A1* | 4/2022 | Cristache | B25J 13/006 |
| 2022/0225982 | A1* | 7/2022 | Yates | A61B 17/07207 |
| 2022/0234194 | A1* | 7/2022 | Deyle | B25J 18/007 |
| 2022/0387031 | A1* | 12/2022 | Yates | A61B 17/07207 |

FOREIGN PATENT DOCUMENTS

| | | | | |
|---|---|---|---|---|
| CA | 3068216 | A1* | 12/2007 | ......... A61B 1/00156 |
| CN | 102688129 | A | 9/2012 | |
| CN | 102892376 | A* | 1/2013 | ......... A61B 1/00135 |
| CN | 107283436 | A | 10/2017 | |
| CN | 108227506 | A | 6/2018 | |
| CN | 207874211 | U | 9/2018 | |
| CN | 109259863 | A* | 1/2019 | ......... A61B 17/1604 |
| CN | 109397245 | A | 3/2019 | |
| EP | 3797715 | A1* | 3/2021 | ............ A61B 17/14 |
| EP | 3505079 | B1* | 12/2021 | ............ A61B 17/068 |
| GB | 2345051 | A* | 6/2000 | ............... A61G 7/10 |
| GB | 2509814 | A* | 7/2014 | ............ B25J 11/009 |
| GB | 2527207 | A* | 12/2015 | ............ B25J 11/009 |
| JP | 2008119820 | A* | 5/2008 | |
| JP | 2008260117 | A* | 10/2008 | |
| KR | 20110054850 | A* | 5/2011 | ............... B25J 5/00 |
| KR | 20120126934 | A* | 11/2012 | ............... B25J 5/00 |
| KR | 101819531 | B1* | 1/2018 | ............ A61B 19/00 |
| KR | 101872282 | B1* | 6/2018 | ............ B62B 5/0043 |
| WO | WO-2007050407 | A1* | 5/2007 | ............... B60T 7/22 |
| WO | WO-2011076240 | A1* | 6/2011 | ............... A61H 1/02 |
| WO | WO-2012149446 | A2* | 11/2012 | ............ B25J 11/002 |
| WO | WO-2012166517 | A1* | 12/2012 | ............ A61B 17/068 |
| WO | WO-2014122752 | A1* | 8/2014 | ............... A61G 5/14 |
| WO | WO-2015137040 | A1* | 9/2015 | ............ A61B 34/30 |
| WO | WO-2016042704 | A1* | 3/2016 | ............... A61G 5/14 |
| WO | WO-2018063100 | A2* | 4/2018 | ......... B25J 11/0055 |
| WO | WO-2020214787 | A1* | 10/2020 | ............ A61G 12/00 |

\* cited by examiner

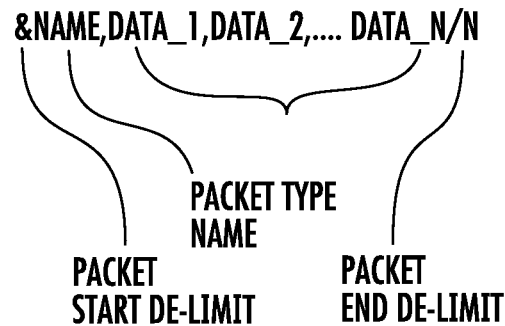

&NAME,DATA_1,DATA_2,.... DATA_N/N
- PACKET TYPE NAME
- PACKET START DE-LIMIT
- PACKET END DE-LIMIT

FIG. 16

| CONTROL .MSG | PERIPHERAL .MSG |
|---|---|
| *HEADER<br>STRING NAME<br>INT    NUMBER_MEMBERS<br>INT[]  DATA_TYPES<br><br>FLOAT[]  FLOAT_MEMBERS<br>STRING[] STRING_MEMBERS<br>INT[]    INT_MEMBERS | *HEADER<br>STRING NAME<br>INT    NUMBER_MEMBERS<br>INT[]  DATA_TYPES<br><br>FLOAT[]  FLOAT_MEMBERS<br>STRING[] STRING_MEMBERS<br>INT[]    INT_MEMBERS |

FIG. 17

```
# ESSENTIAL SERIAL PORT INFORMATION
<SERIAL>
   <COM>/DEV/TTYACM0
   <BAUD>115200

<CONTROL>
   <DEVICE_NAME>RELAYA
   <NUM_PARAMETERS>3
   <DATA_TYPES>2,2,2

<PERIP>
   <PERIP_NAME>BLOCK_1
   <NUM_READINGS>14
   <DATA_TYPES>2,2,2,2,2,2,2,0,0,0,0,0,0,2
   <UNITS>
BOOL, BOOL, RANGE, RANGE, RANGE, ADC_RAW, ADC_RAW, ROLL, PITCH, YAW, ACCX,
ACCY, ACCZ, TEMPERATURE
```

FIG. 18

ADAPTIVE ROBOTIC NURSING ASSISTANT

CROSS-REFERENCE TO RELATED APPLICATIONS

This application is a United States National Phase Entry of PCT International Patent Application No. PCT/US2020/028472, filed Apr. 16, 2020, incorporated herein by reference in its entirety and which claims the benefit of U.S. Provisional Application Ser. No. 62/834,689, filed Apr. 16, 2019, the disclosure of which is incorporated herein by reference in its entirety.

STATEMENT OF GOVERNMENT INTEREST

This invention was made with government support under Grant Nos. 1643989 and 1849213 awarded by the National Science Foundation (NSF). The government has certain rights in the invention.

TECHNICAL FIELD

This specification relates generally to robotics and in particular to an adaptive robotic nursing assistant for physical tasks and patient observation and feedback.

BACKGROUND

Bureau of Labor 2010 statistics indicate almost 3 million registered nurses are currently employed in the United States, making nurses the largest pool of healthcare providers in the country. However, much nursing time is spent on fetching, lifting, and organizing spatially, as well as on repetitive measurements of patients' vital signs, and documentation in electronic medical records of patients. Service robots aimed at improving the performance of this large labor pool have the potential to free nurses to pursue more meaningful interactions, such as counseling patient and family education, which will result in increased patient satisfaction with healthcare.

SUMMARY

This specification describes an adaptive robotic nursing assistant for physical tasks and patient observation and feedback. In some examples, the adaptive robotic nursing assistant includes an omni-directional mobile base robot or platform; a footrest on the omni-directional mobile platform; an instrumented handlebar located above the footrest such that a user standing on the footrest can grasp the handlebar; a display above the handlebar and at least one user input device; a robot manipulator comprising a robotic arm and an end-effector on the robotic arm; and a control system coupled to the omni-directional mobile platform and robotic arm, the control system comprising at least one processor and memory storing executable instructions for the at least one processor to control the omni-directional mobile robot and robotic arm.

In some examples, the display can be a tablet and the input device can be a touch screen, configured for displaying information and receiving user input. The interface may have a microphone to allow receiving voice commands from a user. The interface may also have network and Internet connectivity, which can be useful, e.g., for wireless/remote communication with the robot, live video feeds, and other operations. In some examples, the mobile robot base includes a lift mechanism configured for raising and lowering the robot manipulator.

The computer systems described in this specification may be implemented in hardware, software, firmware, or any combination thereof. In some examples, the computer systems may be implemented using a computer readable medium having stored thereon computer executable instructions that when executed by the processor of a computer control the computer to perform steps. Examples of suitable computer readable media include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF DRAWINGS

FIG. 16 illustrates a transport-layer packet structure.

FIG. 17 shows ROS messages corresponding to Controls and Peripherals.

FIG. 18 shows an example of the configuration file for building a set of publishers and subscribers in the ROS bridge node, structured so that each message does not require a custom MSG definition in ROS.

DETAILED DESCRIPTION

Figure 1A:
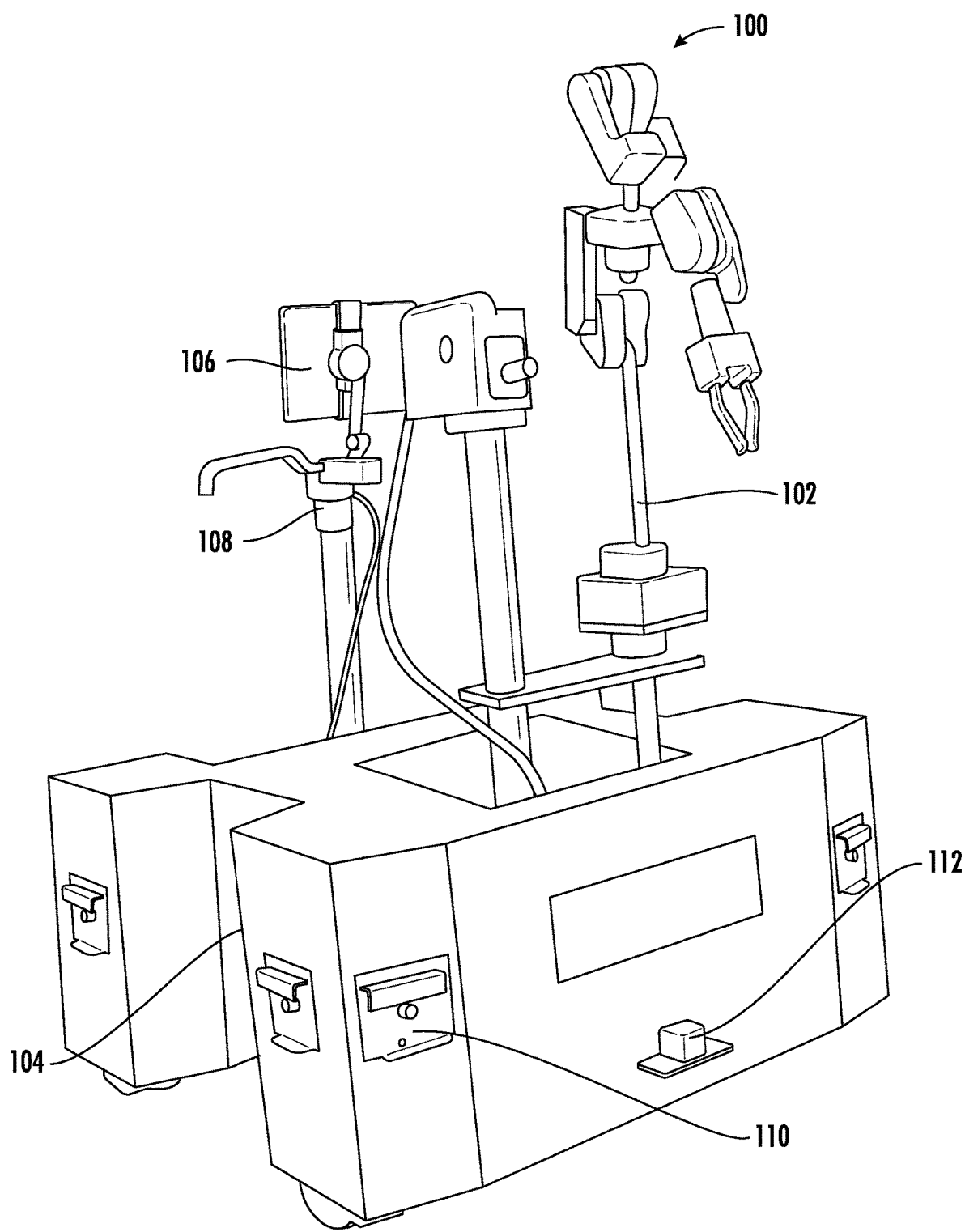
FIGS. 1A-1D illustrate an example implementation of an ARNA robot.

This specification describes methods and systems for an adaptive robotic nursing assistant (ARNA). The ARNA can be used, e.g., for physical tasks and patient observation and feedback.

Robotic performance of routine nursing tasks has the potential to free nurses to pursue more meaningful interactions, which will result in increased patient satisfaction with healthcare. The impact of the ARNA robot performing routine, uncomplicated care tasks or assisting nurses to perform more complex tasks bears substantial impact on efficiency in acute-care hospital environments. The ARNA robot been envisioned to enhance the productivity of nursing staff through robot cooperation during physical and non-physical tasks.

The methods and systems will be described with reference to three studies that follow: a first study, titled "ARNA, a service robot: System overview and User acceptability," and a second study, titled "Neuroadaptive Controller for Physical Interaction with an Omni-Directional Mobile Nurse Assistant Robot," and a third study, titled "ROSFuse: A High-modularity ROS to Firmware Instrumentation Bridge for Robotic Sensors." The examples presented in these studies are provided for purposes of illustration and not limitation.

ARNA, a Service Robot: System Overview and User Acceptability

Using robots capable of collaboration with humans to complete physical tasks in unstructured spaces is a new and rapidly growing approach for future of work. Particular examples where increased levels of automation can increase productivity include robots used as nursing or manufacturing floor assistants. Another example of use is for patient observation and item fetching during a pandemic such as COVID-19 outbreak, in which nursing staff should be protected as much as possible by limiting their physical contact with infected patients. We present a mobile manipulator designed for service as a nurse assistant in hospital environments to assist staff with patient walking and patient sitting tasks. The Adaptive Robotic Nursing Assistant (ARNA) robot consists of an omnidirectional base with an instrumented handlebar, and a 7-DOF robotic arm. We describe the novelties in its mechanisms, controller and instrumentation, and present results from user experiments with human subjects in a simulated hospital environment that demonstrate its usability and ease of use.

1 Introduction

According to the International Federation for Robotics (IFR), with an average year-on-year growth rate of 21% between 2017 and 2021 of sales of service robots, robots that support a human in providing a service as opposed through automation, these robots are in high demand [1]. Of the varied fields in which service robots are used, those used in manufacturing—including Autonomous Ground Vehicles (AGVs) for logistics support and inspection and maintenance—and medical robots for assisted surgery, physical therapy and rehabilitation have the fastest growth with 41% and 50% increase in their sales between 2017 and 2018. Service robots for use in domestic environment are also another notably rising group.

This demand for service robots is partially driven by the need for physical Human Robot Interaction (pHRI) capabilities to achieve tasks in a dynamic environment. In addition, safety requirements for human user(s) who are often in close proximity to the robot, service robots often need to be effective in cluttered, unstructured spaces. Some collaborative robots that have been used as service robots in the manufacturing sector include an object fetch and delivery system in a warehouse in [2], a collaborative mobile production assistant in [3] and a part-assembly arm used in [4]. In the healthcare industry, collaborative service robots have been used in the surgeries, patient monitoring and mobility; the latter tasks falling into a category of tasks for a nursing assistant robot [5-7].

One area that is also currently being researched in the field of pHRI with service robot is their usability and acceptability to the human users that have to work closely with these robots. These evaluations often provide areas for improvement and reassurance on the design and development of service robots. Studies [8-9] are examples of this kind of work done with robots deployed in the manufacturing industry. Some of this kind of work done with service robots in healthcare sector include [10] which analyzes the challenges and benefits of using surgery-assisting robots to both surgeons and overall medical industry, and [6], [11-12] which from different angles, investigate the effects of emotion and touch on the overall attitude of users of physical nursing assistant robots.

We describe work with the Adaptive Robotic Nursing Assistant (ARNA), a service robot capable of providing assistance in collaborative healthcare environments. As the name suggests, the primary user focus is as a nursing assistant in the hospitals, but the design and construction are done with an eye for its eventual use in manufacturing sectors as well.

We present the system description of ARNA, including its mechanisms, control system and sensor interfaces. Novel contributions include a multi-sensor instrumentation board for heteroceptive sensing, a 4-wheel mecanuum system configuration that can operate on uneven or sloped terrain, intuitive tablet control, and a neuroadaptive controller that provides tunable pHRI with users. User experiments were conducted with 24 human subjects, and user experience questionnaires were collected and analyzed. Results of evaluating measures of usability and ease of use indicate that the ARNA robot will find good use in tasks that utilize its primary features.

2 System

Functionally, the ARNA robot has been designed to perform the following functions:

Autonomous navigation in unstructured environments.
Pick and place of certain classes of objects in the environment.
Heteroceptive sensing of environments and human health.
User interface of a physical and teleoperation nature.

The primary tasks which are intended to be achieved by the ARNA robot can be defined as:

Patient sitter: This is a task wherein the robot monitors a user and responds to remote commands. In a hospital room, this can be useful for monitoring bedridden patients for their vitals or providing entertainment and information. It can also be useful during a pandemic such as COVID-19 outbreak, during which direct interaction of nursing staff with patients should be minimized. An item fetch-and-retrieve capability that falls under this task is one that can be used by a bedridden patient.

Patient walker: In this mode, the robot provides ambulatory and bracing support for a patient that requires physical assistance to stand up, walk, and sit down. The robot can help transport objects—by holding or dragging them with the arm gripper (such as IV pole, an oxygen tank, heavy medical equipment, or part on a wheeled platform) or having the object otherwise attached to the base mobile platform (such as a hospital bed). During physical interaction while a user can cooperatively control the motion of ARNA while walking behind it or by riding on the footrests attached to the mobile platform.

2.1 Hardware Platform

FIG. 1A shows an example implementation of the ARNA robot 100. It is a mobile robot equipped with a robotic arm 102, e.g., a 6-DOF or 7-DOF arm. Constructed in-house and designed to be able to transport heavy loads, it has a base footprint of 1.14 m×1.14 m and weighs 226.7 kg.

The robot 100 includes an omni-directional mobile platform 104 that uses 4 mecanum wheels to provide a capability for omni-directional motion, a feature that is useful in the unstructured spaces that the robot is envisioned to be used in. The robot wheels are also connected with a spring suspension that allows for its operation on uneven, outdoor terrain. While the arm 102 has a normal reach of 0.8 m, a riser mechanism is used to extend the effective reach to 1.2 m. The robot 100 also includes a tablet computer 106 (or other appropriate computing device) to present a user interface and a handlebar 108 with at least one force/torque sensor to provide input to the tablet computer 106 and an emergency stop.

Adapters such as those that attach the arm 102 to the riser, and the one that connects the handlebar 108 to the force/torque sensor are designed and implemented to provide a good fit and yet be adaptable for attaching another kind of arm or input interface, as well as connecting the robot 100 for other objects such as a hospital bed, IV pole, or oxygen cylinder that it could be transported when used as patient walker.

The robot 100 can include a sensor system including one or more sensors. As shown in FIG. 1A, the robot 100 includes a number of sensor boxes (e.g., sensor box 110) holding infrared, bump, and ultrasonic sensors. The robot 100 also includes a LiDar sensor 112.

Figure 1B:
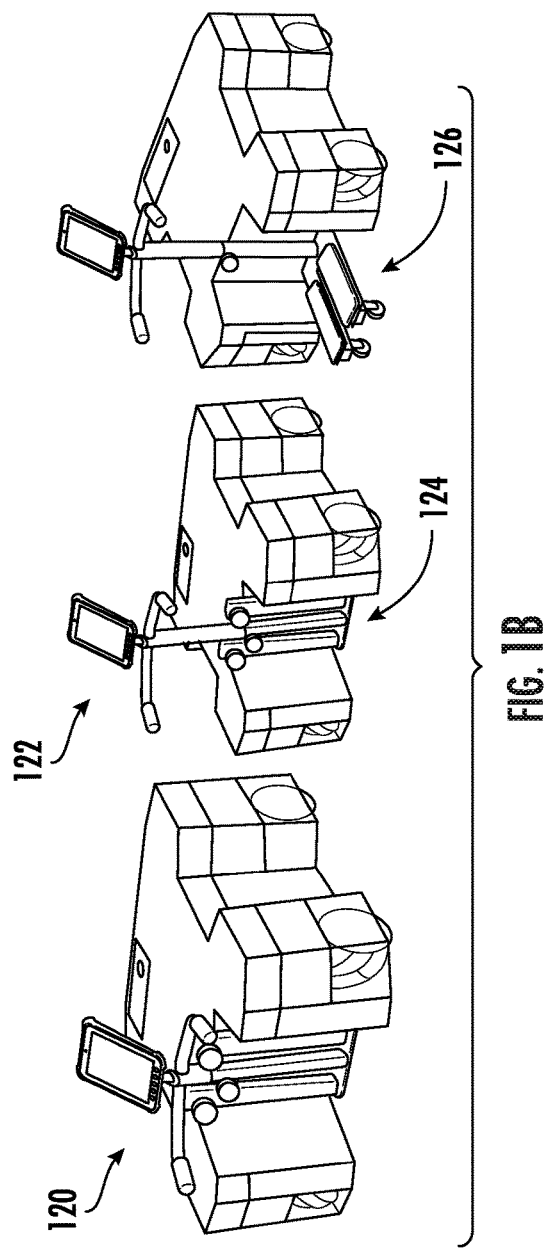
Figure 1C:
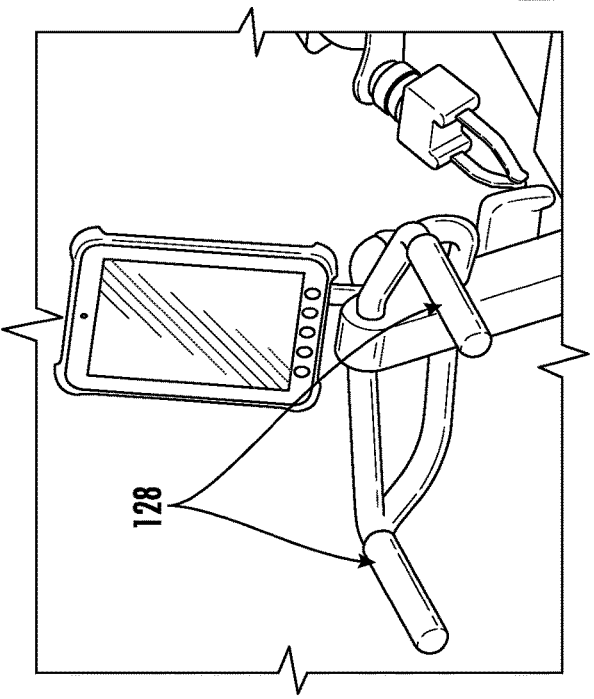
Figure 1D:
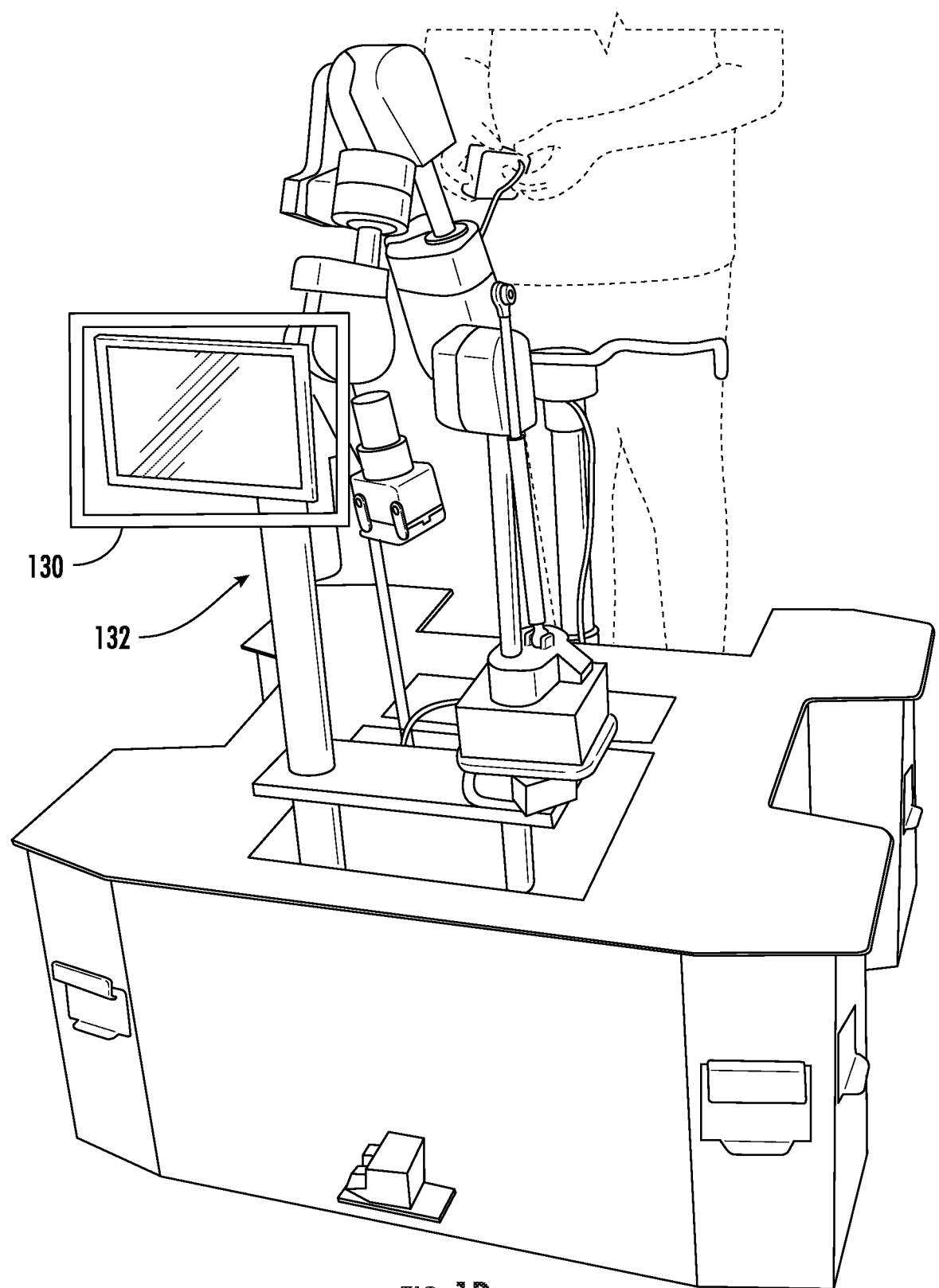

FIG. 1B illustrates the handlebar and footrest. The handlebar is shown in a lowered condition 120 and an elevated condition 122. The footrest can be folded to provide walking space. The footrest is coupled to the omni-directional mobile platform by a hinge to allow folding of the footrest against the omni-directional mobile platform. The footrest is shown in a folded position 124 and a deployed condition 126, and the footrest is shown with castor wheels that can be used to support the footrest while the robot is in motion. FIG. 1C illustrates that the handlebar can be configured with electronic skin 128 to provide further sensor signals to the control system. FIG. 1D shows that the robot 100 can include a display unit 130. at the front of the robot to provide visual instructions and feedback during robot operation. FIG. 1D also illustrates an example a riser mechanism 132 to increase/decrease the operating height of the platform on which the robot manipulator is installed.

In some examples, the robot 100 is configured to capture user gestures using one or more of the following types of sensors: RGB-D Camera (Microsoft Kinect, Asus Xtion Pro), IR Sensor (leap motion), EMG Sensor (Myo Band). The robot 100 can be configured to receive user input through verbal commands using a speech recognition system.

2.2 Instrumentation

Figure 2:
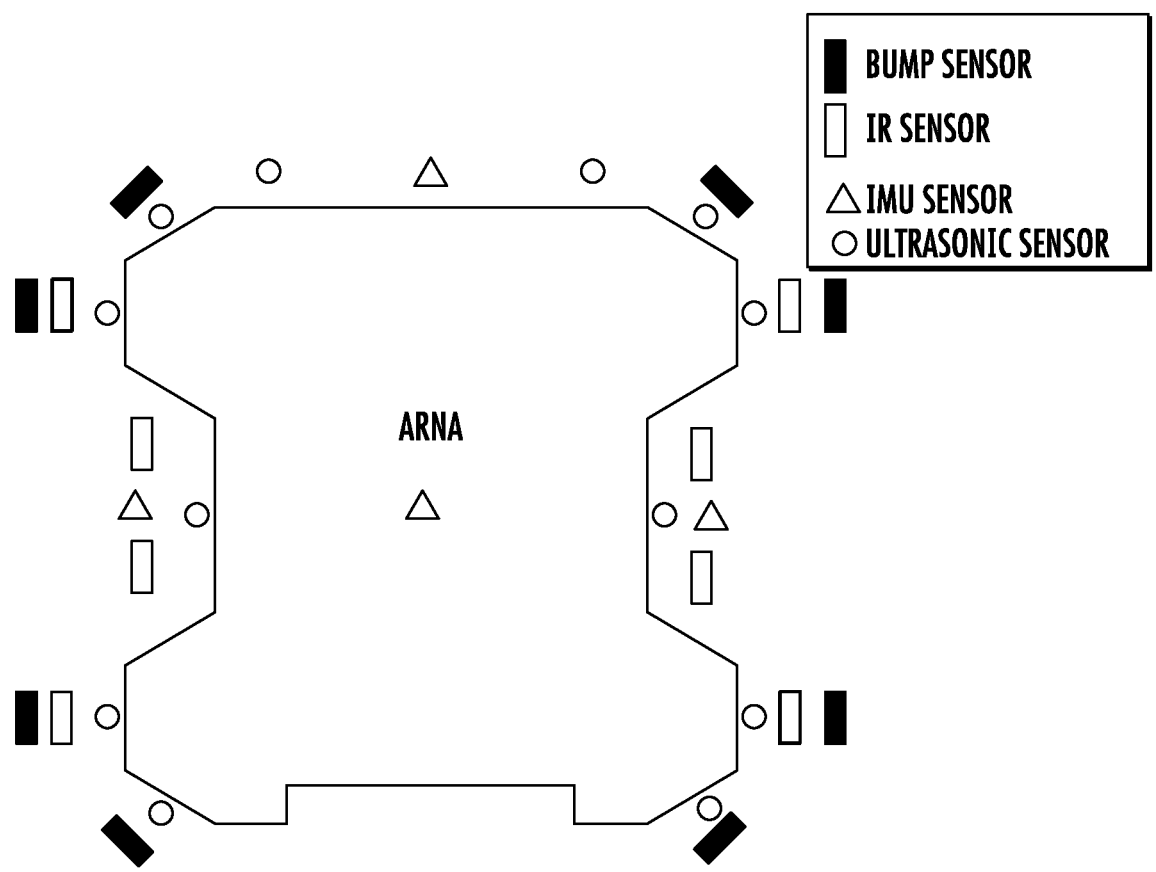
FIG. 2 is a top-view diagram of sensors placed around the ARNA robot. Physically, sensors were installed and wired to modular sensor boxes that include bump, IR, IMU, and ultrasonic units.

A sensor system for environment sensing, early warning and emergency stopping is a key component of the ARNA robot. FIG. 2 shows the sensor suite that has been strategically installed on the robot. This includes 12 ultrasonic sensors distributed around the robot for detecting approaching obstacles. Infrared sensors placed close to the ground act as level sensors are used to detect changing heights of surfaces that the robot is navigating. Imaging sensors include an ASUS Xtion Pro Camera and Hokuyo URG LiDar. Emergency halting of the robot is implemented using bump sensors that when collided with, say by an object suddenly, causes emergency halting system of the robot.

Sensors that facilitate pHRI with the robot include an ATI Axia 80 force-torque sensor that is installed under the handlebar to sense user interaction forces. The adapter for installing this sensor is modular in a way that facilitates quick change for mantane and also using another device for the user to use in interacting with the robot. Another force-torque sensor, Delta model by ATI-IA USA, is installed under the 6-DOF arm of the robot. This has been used for sensing forces and torques in the arm in order to detect collisions and user interaction forces on the arm [13]. Tactile sensors, configured as "robotic skins" can also be deployed on the handlebars of the ARNA robot, or on its robotic manipulator arm, base and end-effector. Examples of robotic skins are described in the following patent application, which is hereby incorporated by reference in its entirety:

SYMMETRIC STRAIN GAUGES FOR PRESSURE SENSITIVE TACTILE SKINS AND ASSOCIATED ACQUISITION, CONDITIONING, AND ENCAPSULATION, PCT/US2018/026478.

Figure 3:
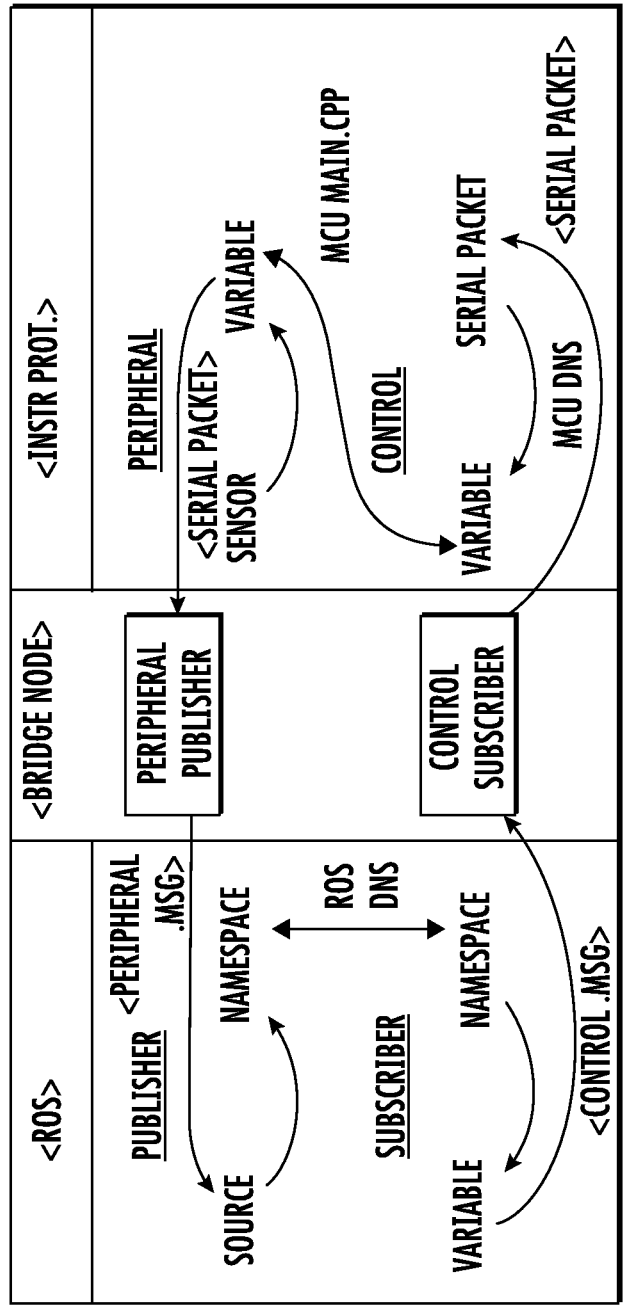
FIG. 3 is a block diagram illustrating an example architecture of a protocol that was implemented to interface serial readout sensors to the robot operating system (ROS).

A component of the ARNA robot is the protocol for reading data with readouts from the IR, ultrasonic and bump sensors. These sensors connect to a microcontroller unit (MCU), which is in turn connected to the robot computing system running Robotics Operating System (ROS). More advanced system-on-chip (SoC) microcontroller/microprocessor units are powerful enough so that they do not need an external computing system to run ROS. A new protocol was developed and implemented to provide a bi-directional asynchronous sensor data over the native hardware USB-Serial. Efficiently designed definition files facilitate packet parsing in both directions—to and from ROS and the MCU—and are used to create individual ROS topics for all available data streams. FIG. 3 below shows the architecture of this protocol and how it is interfaced with ROS through a bridge node.

2.3 Interfaces

Several devices are used to facilitate user interaction with the robot. A joystick/gamepad controller is used for teleoperation purposes, the force-torque sensor equipped under the handlebar as described earlier and an android tablet is used to develop and deploy apps to connect to the robot and issues commands through on-screen buttons and voice commands. The robot is implemented to facilitate a relatively easy hardware and software incorporation of other interfaces like array of skin sensors placed on the handlebar or integrated with a human-located sensor interface like the Myo armband for recognizing activity of a manufacturing worker [14] or rehabilitating patient [15].

The speech processing/synthesizing functionality of the tablet is also leveraged in allowing multimode media presentation to the user, a feature that could make the use of the robot to be more efficient in several modes. Having multiple interfaces allows the robot to be usable by different users depending on their preference/need, which would be quite useful in a hospital with a significantly varied user type.

2.4 Control

Impedance and admittance control strategies are two main approaches to physical interaction with a robot, however, in the conventional application of these methods, the impedance and admittance are constant, and do not adapt to user preferences, user dynamical parameters (for instance mass), user needs and skill level. In contrast, our main approach to control the NAC during physical interaction is the NAC, a Neuroadaptive controller, which is a feedback linearizing control strategy that incorporates machine learning. As presented in the seminal work on NAC in [16], it is a two-loop neural network-based control algorithm with Lyapunov styled proofs of stability.

Compared with the classical PID approach and with the adaptive impedance/admittance control strategies, the NAC is model agnostic to a wide class of robot models, user preferences, and sensor characteristics and requires less effort to tune. There are also works in the literature that shows through experiments that using the NAC to control the robot in pHRI setting causes the user to use lesser effort to achieve an objective when compared with PID [17].

Figure 5:
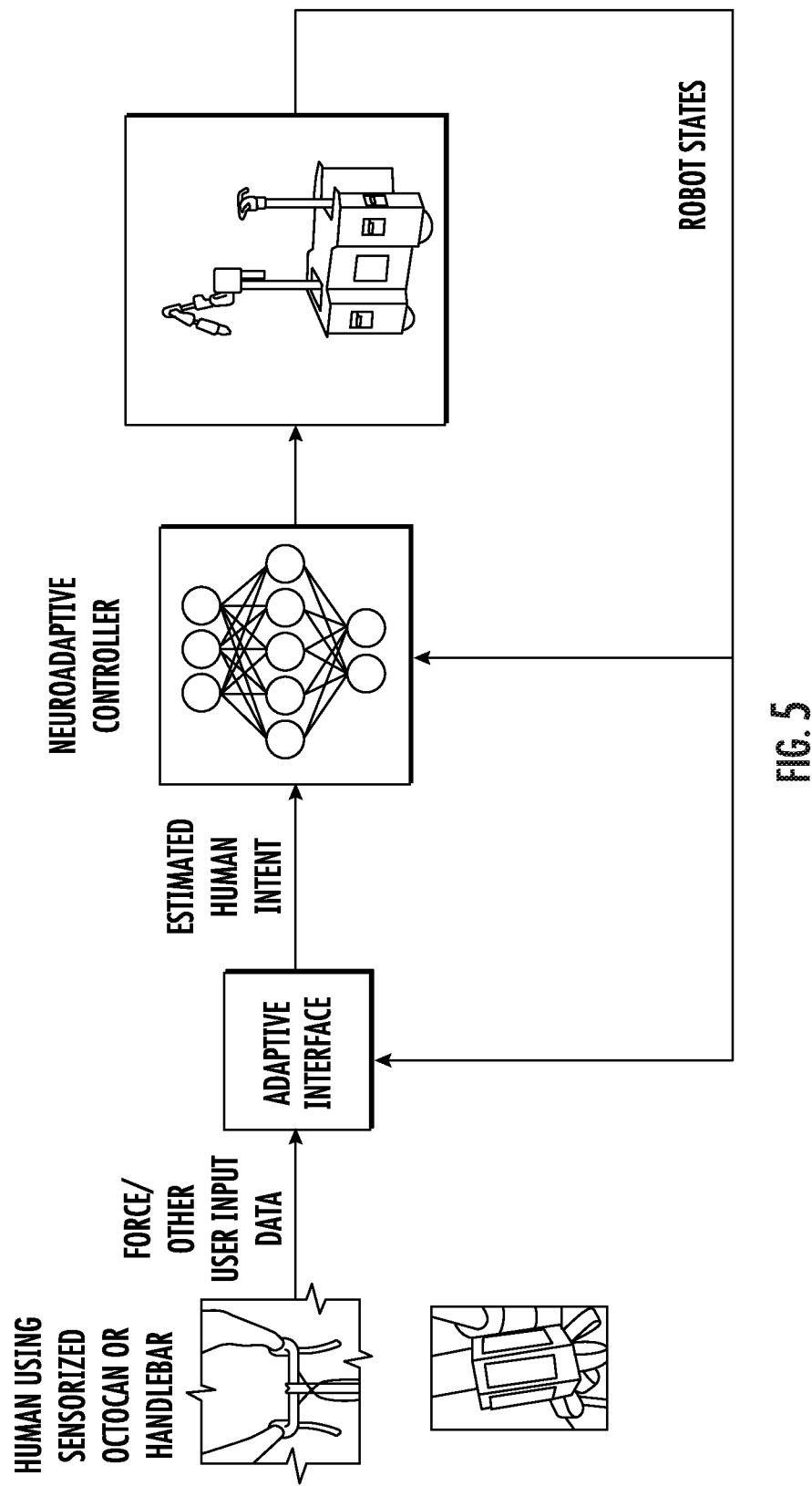
FIG. 5 illustrates ARNA's Impedance control with adaptive interface strategy that uses Neuroadaptive controller as core controller.

The quality of human intent estimation is a critical factor in the perception (and utility provided) by robot in pHRI. the ARNA robot design also uses a Neural network-based approach to estimate human intent as opposed to feeding it directly in the FIG. 5 above.

In taking this strategy in a previous work [18], it was found that using a strategy like this that is similar to NAC resulted in a better overall experience for the user with respect to effort and task completion-based metrics.

For navigation control, we build on implementation and research in [19] which presents work on trajectory generation and obstacle avoidance for the Neptune robot which is a smaller mobile manipulator robot with some of the core components of the ARNA robot.

2.6 Software Architecture

Computing resources on the robot include two single board computers—Nvidia Jetson TX2 and VersaLogic EPU-4562 Blackbird—and a Netgear Nighthawk AC1900 router to provide high-fidelity local network for interfacing and remote control of the robot. Robot Operating System, ROS, framework is the primary implementation platform, which means software development is fundamentally modular and is suited for leveraging useful robotics software that are open-source available.

For different use case scenarios with the ARNA robot, different levels of autonomy would be appropriate. To facilitate the effective usability of the robot for different use cases with different task description and accomplishment requirement, sensor data requirement, we implement software of the ARNA robot using a novel software architecture named Directed Observer Lead Assistant (DOLA) framework.

Figure 6:
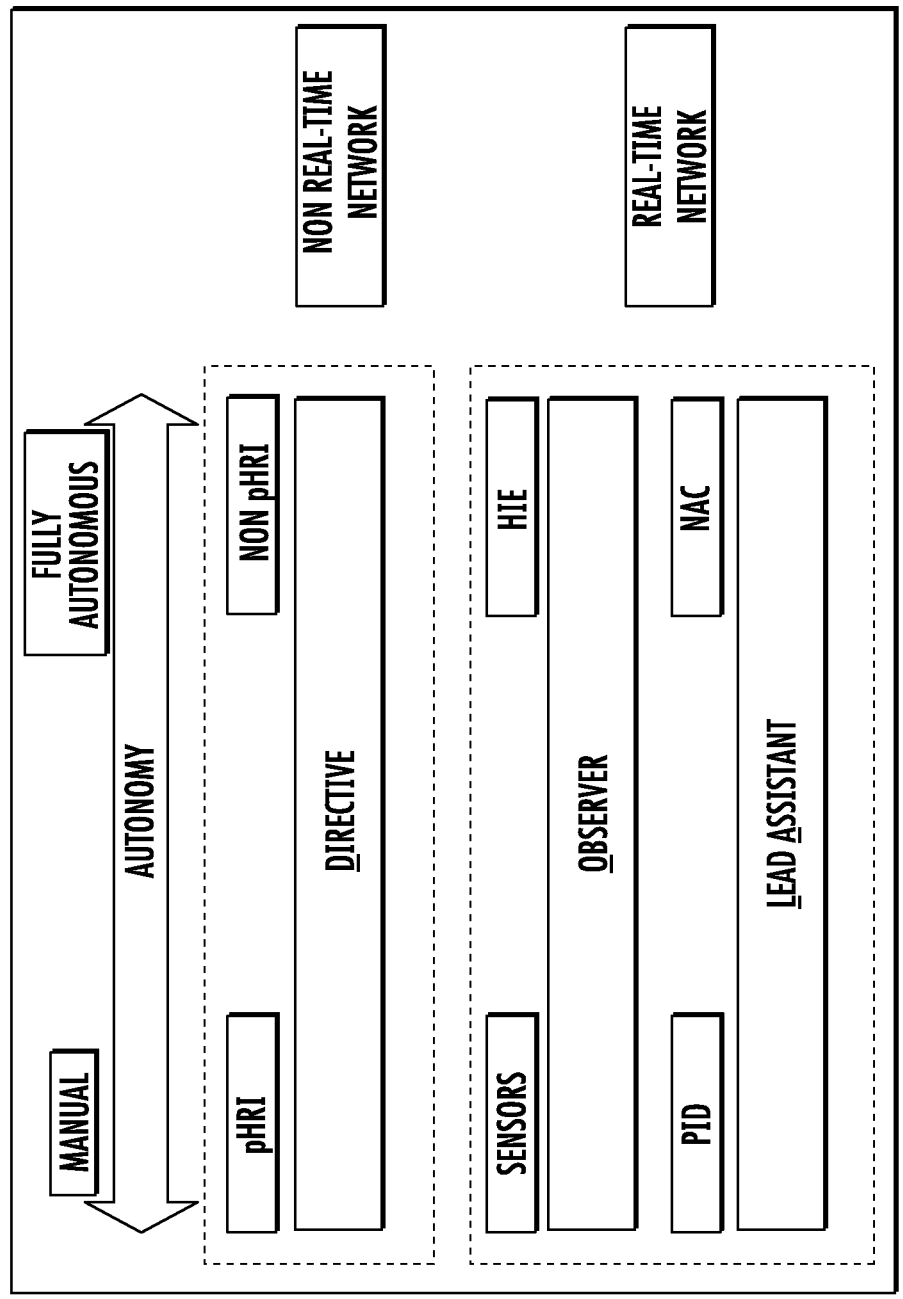
FIG. 6 is a block diagram illustrating an example Directive Observer Lead Assistant (DOLA) software framework used on the ARNA robot to facilitates its functioning in different autonomy levels, from manual to fully autonomous.
Figure 7A:
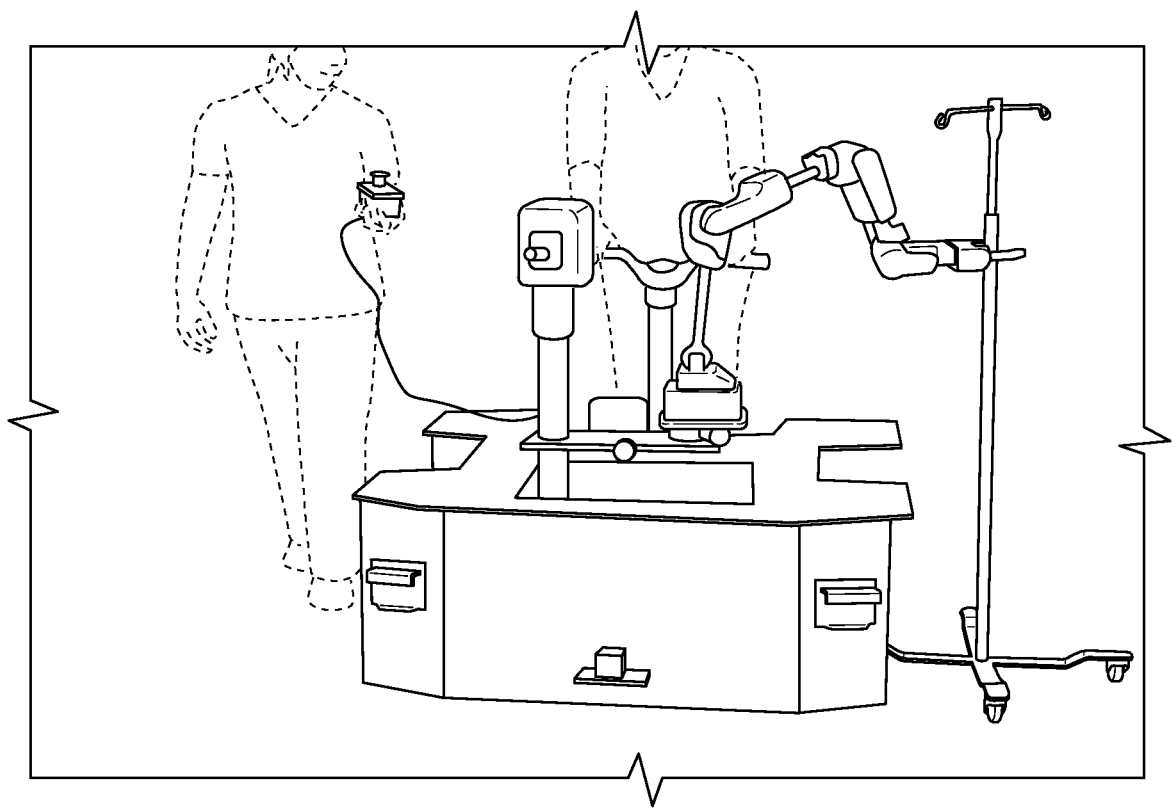
FIG. 7A shows users during a patient walker task experiment in the simulated hospital room.
Figure 7B:
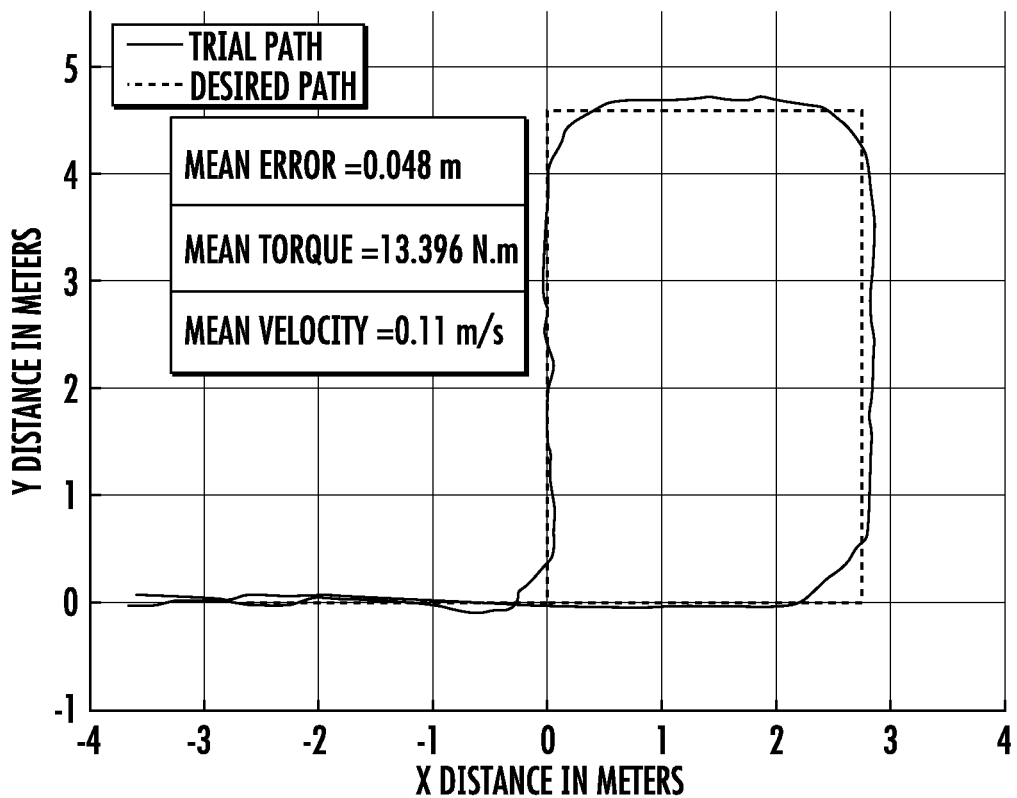
FIG. 7B is a chart illustrating a sample path taken by user during patient walker experiment.

FIG. 6 shows the architecture of the DOLA framework whose three main functional blocks are:
1. Directive: The Directive block defines the user instructions or directives to be followed during any HRI process. The details of the tasks to be performed are stored in this functional block, and data from the human-machine interfaces are included here as user commands.
2. Observer: During HRI, the Observer block monitors the user parameters and estimates the user's intentions in real-time. This ensures safety and facilitates adaptability to different users.
3. Lead Assistant: This block contains real-time controllers for the robot such as the Neuroadaptive controller described in Section 2.5 and low-level PID controllers.

Overall, DOLA is an agile framework that facilitates efficient task completion in the presence of varied use conditions and autonomy levels while maintain safety and usage standards.

3 User Experimentation

ARNA was designed and developed with some input from experienced nurses. While it was at a significant stage in development and could essentially perform the two primary tasks of patient sitting and walking, the robot was tested on by nursing students who are potential nurse users and acted as patients.

The seminal work in [20] presents the Technology Acceptance Model (TAM), a method for analyzing user data collected through Likert-scaled questionnaires in order to predict the Perceived Usefulness (PU) and Perceived Ease of Use (PEOU) of the new technology as part of a set of hypotheses that predict actual use of new technological devices and systems in a certain field. The work presents statistical analysis of how questions with certain themes such as productivity, time use, clarity and controllability correlate with each metric. It has been used in pHRI related works to evaluate human-robot cooperation in production systems [21], care-giving robots [22] and reviewed in [23].

The experiments described in this work were conducted at a hospital room simulation suite located at School of Nursing (SoN), University of Louisville, Kentucky, USA. 5-scale Likert questionnaires were used to calculate the PU and PEOU for the ARNA robot in patient walker and patient sitter scenarios respectively. Average of answers of the respondents under each metric are used as measures of PU and PEOU and are shown in Table 1 and 2 for the walker and sitter experiments respectively.

3.1 Patient Walker

The patient walker task is one where the ARNA robot provides ambulation assistance with stability support. While deployed in a hospital environment for this experiment, with appropriate control paradigm, it is one that can be useful in an industry or home for example to provide ambulation for a factory worker or elderly person in a house needing to get from one point to another while transporting a heavy item.

For these experiments, the user navigated the robot through the handlebar and the arm was used to hold an IV pole. The goal was to have a user—who would be a patient—walk a marked path in the simulated hospital environment with the robot while the robot holds an IV pole. A "nurse" walked alongside the user and robot in a supervisory role while holding an emergency stop to stop the robot should the user and/or robot get into a position that puts them in danger. At the end of the experiment, the "nurses" filled out a Likert scaled questionnaire that was used to evaluate the PU and PEOU of the ARNA robot as a patient walker. In all, there were 24 nurse-patient dyads with 9 trials each involved in the experiments. The 9 trials are 3 trials each of 3 different settings of control gains. Axia is the name of the force/torque sensor through which user efforts were sensed and the settings were named Axia1, Axia2 and Axia3.

The questions asked for Perceived Usefulness of the Patient Walker feature of the ARNA robot are:
1. The robot is responsive to your commands to move in the desired direction (No (1)/Yes (5))
2. I did not often feel like I was going to lose my balance (No (1)/Yes (5))
3. What is the speed of the walker? (Too fast (1)/Too slow (5))
4. I get sufficient stability support from the walker (No (1)/Yes (5))
5. The walker is helpful in completing the walking task (No (1)/Yes (5))
6. I am satisfied with the robot as a mobility aid (No (1)/Yes (5))

For the Perceived Ease of Use evaluation, we asked:
1. The walker is difficult to operate (No (1)/Yes (5))
2. It is easy to learn to use the walker (No (1)/Yes (5))
3. It is easy to avoid bumping into objects (No (1)/Yes (5))

TABLE 1

PU and PEOU metrics for different control settings in the patient walker experiments. Each metric has a minimum score of 1 and maximum of 5

| 1. Metric | 2. Mean | 3. Std. Dev |
|---|---|---|
| 4. PU Axia1 | 5. 3.00 | 6. 1.36 |
| 7. PEOU Axia1 | 8. 3.28 | 9. 1.37 |
| 10. PU Axia2 | 11. 3.06 | 12. 1.30 |
| 13. PEOU Axia2 | 14. 3.33 | 15. 1.38 |
| 16. PU Axia3 | 17. 3.16 | 18. 1.25 |
| 19. PEOU Axia3 | 20. 3.42 | 21. 1.35 |

3.2 Patient Sitter

The patient sitter task is a task that primarily involves the ARNA robot fetching an item for the user. This utility is particularly useful in a nursing assistant robot as fetching items for hospitalized patients is one of the mundane and repetitive tasks performed by nurses and nurse assistant in hospitals. In a manufacturing environment, fetching tools is a sample scenario where this feature can be useful. In its final form, the goal is to enable the ARNA robot to be able to perform this task with different levels of autonomy, from completely autonomous to shared/traded control.

In the experiments whose results are presented here, the task was performed by teleoperation of the robot base and arm through a tablet interface. The teleoperation mode is a useful one—as feedback from the users show—and is a versatile one as it can be applicable in a home or industry. This kind of multi-environment use was in mind during the design and development of the ARNA robot.

Figure 9:
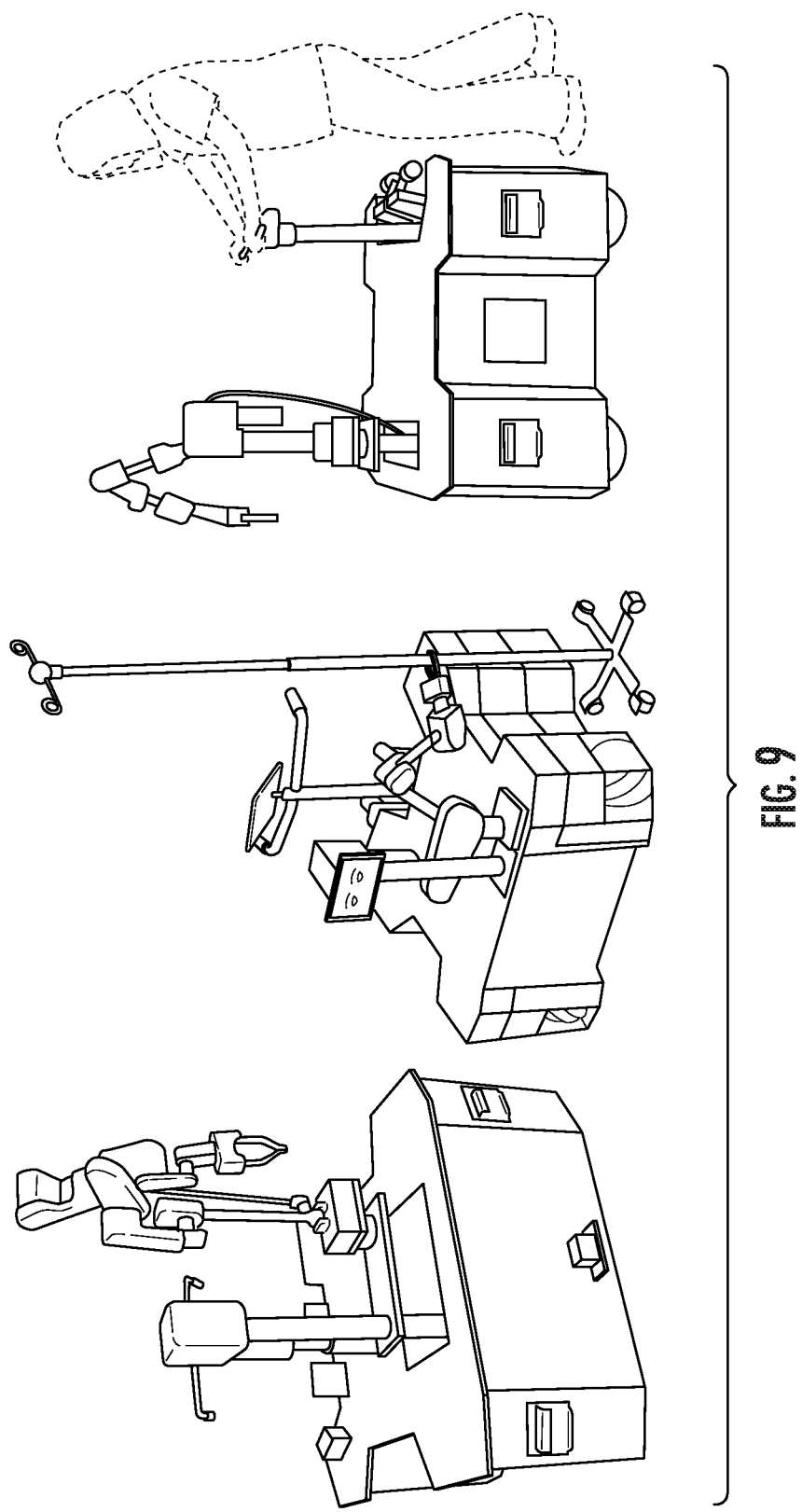
FIG. 9 shows an example Adaptive Robotic Nursing Assistant (ARNA) including an omnidirectional mobile platform, a 6-DOF manipulator, and an instrumented handlebar.

As illustrated in the FIG. 9, the sitter task in these experiments is divided into 4 four parts:
1. Using tablet interface, user teleoperates the ARNA robot to the location of item to be fetched, in this case instruments to take vital measurements.
2. At location of item, the tablet interface is used to teleoperate the arm to fetch the item
3. User teleoperates the ARNA robot to within arm's reach of the user, then collects the item and uses it and returns the item to robot
4. User teleoperates the ARNA robot to return the item to the place it was picked up from.

14 users with 3 trials each were involved in experiments for this task and a summary of results from the session are shown in Table 2.

For Perceived Usefulness of the Patient Sitter function, we asked:
1. How quickly does the robot arrive at its destination using the tablet interface? (Slow (1)/Fast (5))
2. How safe do you think the robot is while you are controlling it with the tablet interface? (Unsafe (1)/Safe (5))
3. What would you say the speed of the robot is when moving around the room? (Slow (1)/Fast (5))
4. How safe do you think the robot is when navigating to the desired place?(Unsafe (1)/Safe (5))
5. How stably did the robot gripper grasp the item? (Unstable (1)/Stable (5))
6. How safe do you think the robot arm is when it hands over the fetched items? (Unsafe (1)/Safe (5))

For Perceived Ease of Use, the questionnaire consisted of:
1. How convenient is it to drive the robot with the tablet interface? (Not convenient (1)/Very convenient (5))
2. How much attention does it take to drive the robot to the desired place while avoiding obstacles? (High (1)/Low (5))
3. How easy is it to drive the robot to the desired place while avoiding obstacles? (Difficult (1)/Easy (5))

4. How convenient is it to tell the robot where to go using the interface? (Not convenient (1)/Very convenient (5))
5. How easy is it to grab items with the robot arm using the tablet interface?(Difficult (1)/Easy (5))

TABLE 2

PU and PEOU metrics for different control settings in the patient sitter experiments. Each metric has a minimum score of 1 and maximum of 5

| Metric | Mean | Std. Dev |
|---|---|---|
| PU | 3.7566 | 1.1208 |
| PEOU | 2.995 | 1.2188 |

3.3 Analysis of Results

On the ARNA experiments, the measure of averages shown in Tables 1 and 2 were obtained by averaging responses to questions corresponding to each metric. For the walker experiments described in Section 3.1, different control settings in Axia1, Axia2 and Axia3 yielded comparable averages, suggesting the users were able to adapt to controlling the robot in different scenarios. This adaptability came with change in average completion times, trajectory errors and velocities.

For the sitter experiments, average task completion time is 209.52 s, which includes an average object pickup time of 49.66 s. While it might not seem like much, for a bed-ridden user or a worker in the factory for whom movement is significantly inconvenient, this can be a significant saving.

An analysis of variance (ANOVA) was carried out on the results on the questionnaire along PU and PEOU lines.

With a p-value<0.0008 in the tested controller setting scenarios, the hypothesis of PU depending on PEOU as presented in the TAM model is found to be true. A $R^2$ values indicate the fraction of the PU values that is dependent on the PEOU values. For the sitter scenario, PU had a 27.2% dependence on PEOU (i.e. $R^2$=0.272) with a p-value of 3.1e−05.

TABLE 3

PU and PEOU metrics for different control settings in the patient walker experiments.

| | Controller setting | | |
|---|---|---|---|
| | Axia1 | Axia2 | Axia3 |
| Average completion time (s) | 101.73 | 92.0 | 91.36 |
| Average Trajectory error (m) | 0.57 | 0.47 | 0.43 |
| Average velocity (m/s) | 0.21 | 0.22 | 0.225 |

TABLE 4

Statistical analysis of dependence of PEOU on PU.

| Independent variable | Dependent variable | p-value | $R^2$ |
|---|---|---|---|
| PEOU Axia1 | PU Axia1 | 2.37e−06 | 0.308 |
| PEOU Axia2 | PU Axia2 | 0.0008 | 0.171 |

TABLE 4-continued

Statistical analysis of dependence of PEOU on PU.

| Independent variable | Dependent variable | p-value | $R^2$ |
|---|---|---|---|
| PEOU Axia3 | PU Axia3 | 0.0001 | 0.209 |

4 Discussion

While primarily targeted for use in the medical industry, the design and implementation of the ARNA robot—its subsystems and their integration—facilitate its use in other unstructured and cluttered environment. Its primary functional capabilities of patient walking and patient sitting are implemented to make them adaptable to different applications in healthcare as well as in other industries such as the manufacturing industry. For example, patient walking described in the user tests in Section 3 above wherein the robot provides patient ambulation support, can be configured to provide physical rehabilitation assistant through setting the Human Intent Estimator module to enforce a desired prescribed motion dynamic that facilitates appropriate physical rehabilitation of the user.

Another example of adaptable use of the ARNA robot is the use of the robot arm. In patient sitter scenario, the arm is remotely operated to fetch items. As presented in [13], by having a force-torque sensor installed under the arm, human interactions and collisions with the arm can be detected. This is a feature that would be of essential use in a pHRI-capable service robot for part assembly alongside a human as well as in other interesting applications on a manufacturing floor. Having a riser mechanism that gives the arm and extended vertical reach is a feature that allows it to be used in object picking in an industrial setting.

In general, the adaptable mechanisms of the ARNA robot, the use of a neural network based control strategy and a novel low-latency instrumentation protocol that fits well into the novel DOLA software architecture in the ARNA robot means there are good foundations for the deployment of the robot for use in different applications with different autonomy levels.

The user acceptability studies carried out show that usefulness and ease of use of the ARNA robot's core functionalities of walking and sitting as are currently implemented are well accepted in a hospital environment. While this study was done in a simulated—not actual—hospital room and could use more users, the built-in capability for extending the robot such as varied interface adapters and configuration of the robot provide a good foundation for relatively easy to improvement of the robot to adapt to varied environment while maintaining/improving its user acceptability ratings. In future work, we intend to conduct longitudinal studies with such features implemented with actual potential users in hospitals and factories. These studies would be done with a goal of doing a more complete TAM analysis of the ARNA robot by using improved TAM models such as those in [23].

5. Conclusion

We presented an overview of the functional subsystems of the ARNA robot, a service robot configured as a mobile manipulator for pHRI. The novelty of this robot consists in mechanical design subsystems, its neuroadaptive control system and interface, and in its sensing instrument protocol. Experimental results from a cohort trial with 24 human subjects are presented and results of preliminary user studies that show the robot's usability as a service robot. In particular, results indicate good usefulness and ease of use of the essential sitter and walker features of the robot. While its primary design target is for use in a hospital, ARNA can also be used for part fetching, transport and manipulation in a manufacturing Environment.

REFERENCES

[1] International Federation of Robotics. 2019. World Robotics Service Robot Report. https://ifr.org/ifr-press-releases/news/service-robots-global-sales-value-up-39-percent

[2] Wise, Melonee, Michael Ferguson, Derek King, Eric Diehr, and David Dymesich. 2016. Fetch and freight: Standard platforms for service robot applications. *Workshop on autonomous mobile service robots.* 2016.

[3] https://www.staubli.com/en-us/robotics/product-range/mobility/helmo-mobile-robot-system/HelMo the mobile robot system

[4] Tlach, Vladimir, Ivan Kuric, Zuzana Ságová, and Ivan Zajačko. Collaborative assembly task realization using selected type of a human-robot interaction. *Transportation Research Procedia* 40 (2019): 541-547.

[5] Shademan, Azad, Ryan S. Decker, Justin D. Opfermann, Simon Leonard, Axel Krieger, and Peter C W Kim. Supervised autonomous robotic soft tissue surgery. *Science translational medicine* 8, no. 337 (2016): 337ra64-337ra64.

[6] Ding, Ming, Ryojun Ikeura, Yuki Mori, Toshiharu Mukai, and Shigeyuki Hosoe. 2013. Measurement of human body stiffness for lifting-up motion generation using nursing-care assistant robot—RIBA. *IEEE SENSORS*, pp. 1-4. IEEE. 2013

[7] Niechwiadowicz K. and Khan Z. 2008. Robot based logistics system for hospitals-survey. *IDT Workshop on interesting results in computer science and engineering.*

[8] Bakajic, Maria, Theresa Becker, and Saana Boahen. 2013. An analysis of participants' experiences of HELMO workshops. *Laurea University of Applied Sciences Otaniemi.*

[9] Markis Alexandra, Maximilian Papa, David Kaselautzke, Michael Rathmair, Vinzenz Sattinger, and Mathias Brandstötter. 2019. Safety of Mobile Robot Systems in Industrial Applications. *Proceedings of the ARW & OAGM Workshop* 2019.

[10] Enayati, Nima, Elena De Momi, and Giancarlo Ferrigno. 2016. Haptics in robot-assisted surgery: Challenges and benefits. *IEEE reviews in biomedical engineering* 9 (2016): 49-65.

[11] Vsnni, K. J. and S. E. Salin. 2019. Attitudes of Professionals Toward the Need for Assistive and Social Robots in the Healthcare Sector. *Social Robots: Technological, Societal and Ethical Aspects of Human-Robot Interaction.* Springer. p. 205-236.

[12] Li Jamy Jue, Wendy Ju, and Byron Reeves. 2017. Touching a mechanical body: tactile contact with body parts of a humanoid robot is physiologically arousing. *Journal of Human-Robot Interaction* 6, no. 3 (2017): 118-130

[13] Sumit K. Das, Indika Wijayasighe, Mohammad Nasser Saadatzi, and Dan O. Popa. 2018. Whole body human-robot collision detection using base-sensor neuroadaptive interaction. *IEEE 14th International Conference on Automation Science and Engineering (CASE)*, pp. 278-283. IEEE, 2018.

[14] Tao Wenjin, Ze-Hao Lai, Ming C. Leu, and Zhaozheng Yin. 2018. Worker activity recognition in smart manufacturing using IMU and sEMG signals with convolutional neural networks. *Procedia Manufacturing* 26 (2018): 1159-1166.

[15] Sathiyanarayanan, Mithileysh, and Sharanya Rajan. MYO Armband for physiotherapy healthcare: A case study using gesture recognition application. 2016. *8th International Conference on Communication Systems and Networks (COMSNETS)*, pp. 1-6. IEEE, 2016.

[16] Frank L. Lewis, Suresh Jagannathan, and Aydin Yesildirek. 1999. *Neural Network Control of Robot Manipulators and Nonlinear Systems.* Taylor and Francis, London, 1999.

[17] Ranatunga Isura, Sven Cremer, Frank L. Lewis, and Dan O. Popa. 2015. Neuroadaptive control for safe robots in human environments: A case study. *IEEE International Conference on Automation Science and Engineering (CASE)*, pp. 322-327. IEEE, 2015.

[18] Cremer Sven, Sumit Kumar Das, Indika B. Wijayasinghe, Dan O. Popa, and Frank L. Lewis. 2019. Model-Free Online Neuroadaptive Controller With Intent Estimation for Physical Human-Robot Interaction. *IEEE Transactions on Robotics* (2019).

[19] Ranatunga, I., & Popa, D. O. (2012, June). Collision-free trajectory generation on assistive robot Neptune. *Proceedings of the 5th International Conference on PErvasive Technologies Related to Assistive Environments (PETRA '12)* (pp. 1-6).

[20] Davis Fred D., Richard P. Bagozzi, and Paul R. Warshaw. 1989. User acceptance of computer technology: a comparison of two theoretical models. *Management science* 35, no. 8 (1989): 982-1003.

[21] Bröhl Christina, Jochen Nelles, Christopher Brandl, Alexander Mertens, and Christopher M. Schlick. 2016. TAM reloaded: a technology acceptance model for human-robot cooperation in production systems. *International conference on human-computer interaction*, pp. 97-103. Springer, Cham, 2016.

[22] Mitzner Tracy L., Charles C. Kemp, Wendy Rogers, and Lorenza Tiberio. 2013. Investigating healthcare providers' acceptance of personal robots for assisting with daily caregiving tasks. *CHI'13 Extended Abstracts on Human Factors in Computing Systems*, pp. 499-504. 2013.

[23] Lai PC. 2017. The literature review of technology adoption models and theories for the novelty technology. *JISTEM—Journal of Information Systems and Technology Management* 14, no. 1 (2017): 21-38.

Neuroadaptive Controller for Physical Interaction with an Omni-Directional Mobile Nurse Assistant Robot Robot-assisted healthcare could help alleviate the shortage of nursing staff in hospitals and is a potential solution to assist with safe patient handling and mobility. In an attempt to off-load some of the physically-demanding tasks and automate mundane duties of overburdened nurses, we have developed the Adaptive Robotic Nursing Assistant (ARNA), which is a custom-built omnidirectional mobile platform with a 6-DoF robotic manipulator and a force sensitive walking handlebar. We present a robot-specific neuroadaptive controller (NAC) for ARNA's mobile base that employs online learning to estimate the robot's unknown dynamic model and nonlinearities. This control scheme relies on an inner-loop torque controller and features convergence with Lyapunov stability guarantees. The NAC forces the robot to emulate a mechanical system with prescribed admittance characteristics during patient walking exercises and bed moving tasks. The proposed admittance controller is implemented on a model of the robot in a Gazebo-ROS simulation environment, and its effectiveness is investigated in terms of online learning of robot dynamics as well as sensitivity to payload variations.

I. Introduction

According to the US Bureau of Labor Statistics [1], registered nurses will be the largest labor pool in the US by 2022, and more than 1.1 million nursing positions have to be filled by then in order to avoid additional shortage. Robots are a potential solution in healthcare environments to assist with safe patient handling and mobility and, thereby reducing the likelihood of workplace injuries. In recent years, robots have been used in hospitals to assist with surgical procedures, to deliver medications, to monitor patients, and to assist with daily hygiene [2]. For instance, nursing assistant robots with a human form factor have been employed to provide patient lift assistance to nurses and, hence, prevents lifting-related musculoskeletal injuries [3]. Similarly, Trina which is a remote-controlled anthropomorphic robot placed on a wheeled mobile base, has been developed to perform mobile manipulation tasks such as bringing food and medication, as well as cleaning in quarantine areas [4]. Other endeavors in the literature to assist nursing staff with physical tasks in healthcare environments include robotic patient lift and transfer [5] and robot-assisted dressing of patients [6].

In an attempt to off-load some of the physically-demanding tasks and automate mundane low-level duties of overburdened nurses, we have developed the Adaptive Robotic Nursing Assistant, ARNA, which is a service robot capable of navigating in cluttered hospital environments and performing automated nursing tasks. ARNA is a heavy-duty omnidirectional mobile robot constructed in-house with a customized 6-DoF robotic manipulator (FIG. 9). We have developed a physical human-robot interaction (pHRI) strategy for the ARNA robot that interprets the force/torque readings from the instrumented handle bar and controls its motion based on a model-free admittance control scheme.

Admittance and impedance control are popular classes of implicit force control, and have been extensively studied in terms of stability and performance in robotic contact tasks [7, 8]. The preliminary goal in this control technique is to provide a stable contact by the robot's end effector during robot-environment contact or to prepare a natural physical human-robot interaction (pHRI), by regulating the mechanical compliance of the robot [8, 9]. In general admittance control, the tracking error dynamics are forced to follow a prescribed admittance model with virtual mass, stiffness, and damping coefficients, and, thereby enabling the robot to behave compliantly [10-12]. The admittance control technique, however, typically depends on known dynamic model of the robot as well as the robot-environment contact characteristics [13]. In the case of ARNA, however, the system suffers from a highly-perturbed dynamics as the robot is subject to diverse slopes as well as uncertain and heavy payloads (e.g., hospital beds with bariatric patients atop, and riders with unknown weight). Furthermore, these payloads are exerted at different sides of the robot (e.g., heavy bed in the front, human rider at the back, and medical equipment around the robot). Such unbalanced payload distribution results in an unknown, time-varying center of gravity and, ultimately unbalanced load and frictional forces on each actuator. Additionally, nonlinearities caused by inherent flexibility/uncertainty in the handlebar-user linkage increase the overall model's perturbations. In the presence of these inaccuracies, relying on model-based controllers lead to performance deterioration and hence safety hazards (e.g., collision), unless conservatively-high controller gains are employed.

For guaranteed trajectory tracking in robots with nonlinearities and model uncertainties, various adaptive control algorithms have been employed based on, for instance, feedback linearization and computed torque control [14]. There also exist a number of efforts in the literature that successfully implemented neuroadaptive schemes to control robotic manipulators with modeling inaccuracies [15]. The pioneering work by Lewis [13] and colleagues proposed a neural network (NN) controller that tuned parameters of the closed-loop system's error dynamics to approach a desired dynamic model. In recent years, this controller has been effectively deployed on very large multi-degree of freedom humanoid-robots such as the ATLAS [16] and the PR-2 [17].

We propose a robot-specific adaptive admittance controller for the ARNA robot's omnidirectional base that employs NN-based learning to online approximate the robot's unknown model and to cancel out its nonlinearities. This control scheme relies on an inner-loop torque controller that forces the robot to emulate a mechanical system with desired admittance characteristics, with convergence guarantees, in response to operator input forces/moments applied to ARNA's handlebar. The proposed admittance controller, which requires no a priori information about the task or trajectory, enables a consistent performance of the robot from the operator's point of view, despite directional and dynamic nonlinearities of the robot. As such, this controller obviates the need for the operator to learn and compensate for task-specific model and uncertainties of the robot, thereby reducing the operator's cognitive and physical load.

II. System Description

The ARNA robot has been developed to assist nursing staff through cooperation during physical activities (bed and cart pushing, item fetching, etc.) and to improve their productivity through automation of repetitive non-physical tasks (patient observation, vital signs measurements, etc.).

A. Omnidirectional Mobile Platform

Figure 10:
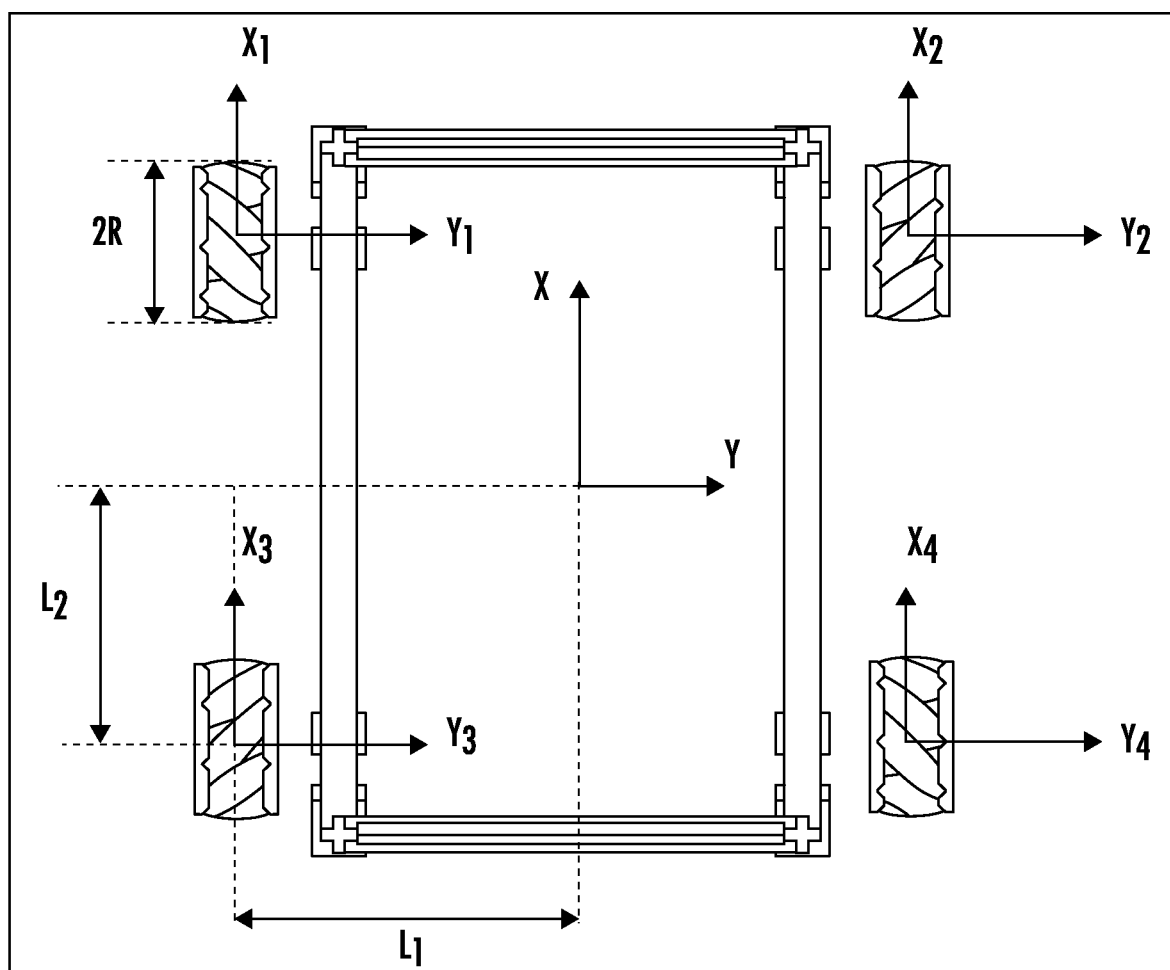
FIG. 10 is a schematic of the mobile platform using Mecanum omni-directional wheels.

ARNA's drive-train is composed of four Mecanum wheels, arranged in a longitudinal symmetrical layout [18], and are driven by four independently-controlled servo motors with angle, velocity, and torque feedback. The servo motors are coupled with the Mecanum wheels through right-angled high-ratio gearboxes, and are mounted to the four corners of the robot chassis (FIG. 10). This drive-train allows omnidirectional mobility and enables simultaneous and independent translational (forward/backward, sideways) and rotational maneuvers from any configuration, obviating the need for non-holonomic path planning and control. Such omnidirectional mobility truly yields the user's navigational intent and is ideal for collision avoidance and navigating through congested hospital corridors in close proximity of humans.

Mecanum wheels are fairly traditional wheels which include a few rollers mounted around their perimeter. The rollers may be installed with various bias angles but they are usually mounted at a 45° angle to the plane of the wheel in contact with the ground. With a zero-roller-ground-slippage assumption, the inverse kinematics of the platform moving on a horizontal plane can be formulated as:

$$V_w = \begin{bmatrix} \omega_1 \\ \omega_2 \\ \omega_3 \\ \omega_4 \end{bmatrix} = J \cdot V = \frac{1}{R} \begin{bmatrix} 1 & 1 & -L_1-L_2 \\ 1 & -1 & L_1+L_2 \\ 1 & -1 & -L_1-L_2 \\ 1 & 1 & L_1+L_2 \end{bmatrix} \begin{bmatrix} V_X \\ V_Y \\ \Omega \end{bmatrix} \quad (1)$$

where Vw is the wheels' velocity vector, J is the Jacobian matrix, $V=[V_X\ V_Y\ \Omega]^T$ is the generalized velocity vector of center point of rotation [19]. In this equation, R is the Mecanum wheel radius, and $L_1$ and $L_2$ are two parameters associated with the layout of the platform as shown in FIG. 10.

B. Instrumented Handlebar

At the rear end of the mobile platform, ARNA incorporates a handlebar. When ARNA is used as an ambulatory assistive device, this handlebar provides a physical support for patients to hold onto and maintain their balance while walking along the robot. In addition, this handlebar serves as ARNA's main human-machine interface (HMI) as it is instrumented with an industrial 6-axis force/torque sensor. When a patient holds onto this handlebar and applies force and moments, ARNA's main control unit interprets the force/torque measurements for his/her navigational intent, and moves the mobile platform accordingly based on an admittance controller scheme (as explained in the following section). This instrumented handlebar, along with the underlying admittance controller, provide an intuitive HMI for ARNA and a natural pHRI between ARNA and its users. Through this handlebar, a nurse can control the robot's motion when, for instance, manually moving heavy items, such as hospital beds and carts.

III. Controller Formulation

Figure 11:
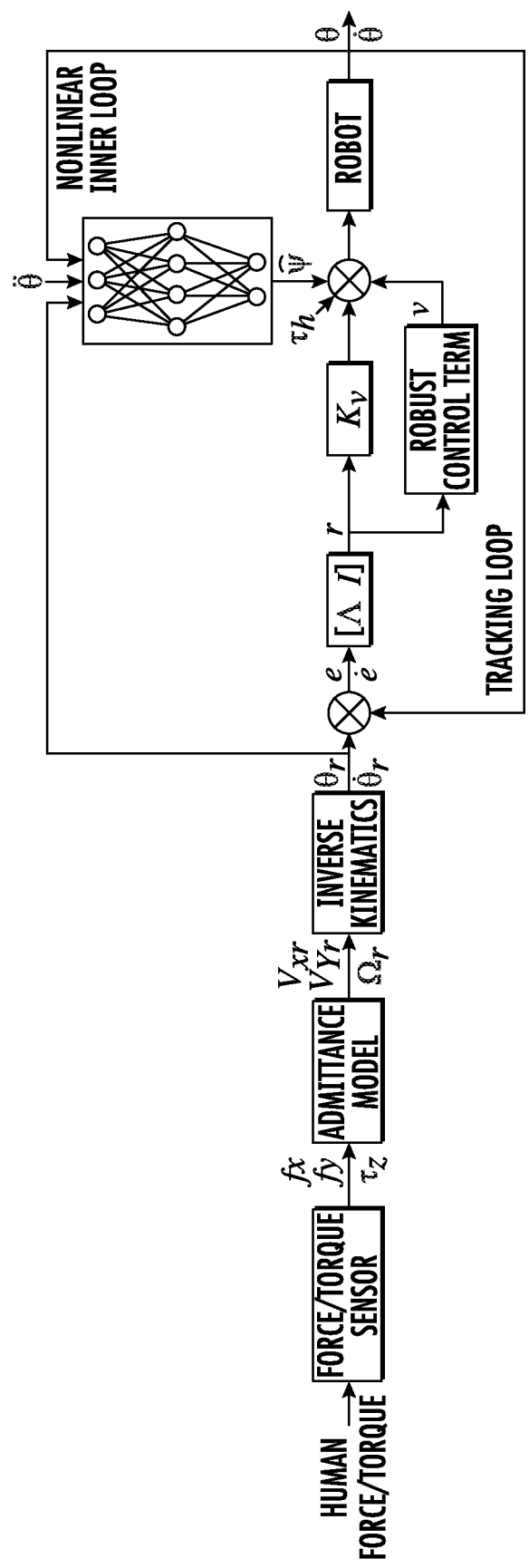
FIG. 11 is a block diagram illustrating an example admittance controller including feed-forward admittance model and inner-loop neuroadaptive controller.

In an admittance controller, the objective is to produce robot's movement in response to sensed forces and torques. Admittance of a compliant mechanical structure is typically represented as a transfer function, G, which is the ratio of the structure's velocity to the forces/torques applied to the structure [20], as $$G(s) = V(s)F^{-1}(s) \quad (2)$$

where F is the input forces/torques, V is the output velocity, and s is the complex frequency. A mechanical structure with a large admittance is easily set in motion with the application of small forces and torques; while a structure with a small admittance requires large acting forces and torques. In this study, an admittance-based interaction control scheme is developed for ARNA's mobile platform. In this scheme, ARNA moves in response to forces and torques applied by a user to its handlebar, and emulates a dynamic system with desired compliant characteristic. As depicted in FIG. 11, this control scheme includes a feed-forward admittance model and a closed-loop neuroadaptive controller. The admittance model generates the reference motion of the mobile platform in response to the human force/torque inputs, which is then converted to reference motion of each wheel using the robot's inverse kinematics given in (1). Finally, the neuroadaptive controller ensures the reference motion of each wheel is tracked, even in the presence of nonlinearities and uncertainties. The neuroadaptive inner-loop controller used in this study does not rely on any information about the feed-forward admittance model, enabling a decoupled design of the task-specific admittance model.

A. Prescribed Admittance Model

ARNA's mobile platform has three degrees of freedom (DoF); longitudinal, lateral, and rotational motions. Therefore, a 3-DoF decoupled mass-damper admittance model was developed for its motion, as below, prescribing its compliance behavior in each respective direction.

$$V(s) = G(s)F(s) = diag(G_x(s), G_y(s), G_\omega(s))F(s) = \quad (3)$$

$$diag\left(\frac{1}{sM_x + D_x}, \frac{1}{sM_y + D_y}, \frac{1}{sM_\omega + D_\omega}\right)\begin{bmatrix}f_x(s)\\f_y(s)\\\tau_z(s)\end{bmatrix}$$

where fx and fy are the forces applied to the handlebar in the x and y directions, respectively, and Tz is the torque in the rotational direction. In this equation, Mi and Di, $i \in \{x, y, \omega\}$, are the virtual inertial and damping coefficients of the admittance model, respectively, that are prescribed to achieve desired characteristics for force-to-motion conversion in each direction. For instance, the steady-state response of the admittance model in the longitudinal direction when a constant force fx is applied to the handlebar is fx/Dx. In other words, to achieve a steady-state forward velocity of $v_{x,ss}$, a constant pushing force of Dx vx,ss is required. Following this logic, the damping coefficients (i.e., Dx, Dy, and Dω), determine the user's burden necessary for a target velocity in different directions. Similarly, the time constant of these transfer functions is Mi/Di, $i \in \{x, y, \omega\}$. Therefore, by adjusting these virtual coefficients, we can alter both transient and steady-state response of the system, and arbitrarily shape the human-robot interaction dynamics. In practice, these design parameters are adjusted such that the velocities reach equilibrium as quickly as possible without oscillation, while minimizing the physical burden on the human user in order to offer maximal power assistance.

Time-domain output of this transfer function in response to the force/torque measurements is solved in real time and set as the desired velocities of the mobile platform. By solving the inverse kinematics of the mobile platform, presented in (1), we can obtain the desired actuator velocities. Such admittance control scheme emulates a dynamic system with a desired, linear behavior, and induces a feeling in the user as if they are interacting with a mechanical system with those prescribed characteristics.

B. Neuroadaptive Controller

The origin of NNs-based system identification and closed-loop control systems goes back to the early 1990s through the seminal work by Narendra and Parthasarathy [21], where multilayer and recurrent networks, along with back-propagation techniques, were successfully used to control nonlinear dynamic systems. Since then, numerous studies have investigated internal stability and tracking performance guarantees of NNs-based control systems [22-24]. In the current study, we extend the neuroadaptive controller initially presented by Lewis and colleagues [15, 23] to ARNA's mobile base in a joint trajectory tracking task. Below the formulation of this neuroadaptive controller, in the joint space, is discussed in short.

The robot's dynamics in the joint space is $$H(\theta)\ddot{\theta} + C(\theta,\dot{\theta})\dot{\theta} + F(\dot{\theta}) + G(\theta) + \tau_d = \tau + \tau_h \quad (4)$$

where θ is the robot's joint angles, H is the inertial/mass matrix, C is the Coriolis matrix, τd is the disturbance vector, τ is the control torque, τh is the user input, and F summarizes the friction forces.

The admittance model block, followed by the robot's inverse kinematics, determines the desired trajectory of each actuator (i.e., in the joint space) in response to the user forces and torques exerted to the ARNA's handlebar. Assuming the reference trajectory in the joint space, θr, is known, the trajectory-following error, e, and the sliding-mode error, r, are defined as $$e = \theta - \theta_r \quad (5)$$

$$r = \dot{e} + \Lambda e \quad (6)$$

where Λ is a symmetric, positive-definite design matrix. Incorporating (5) and (6) in (4), the sliding-mode error dynamics is achieved as $$H(\theta)(\ddot{\theta}_r - \dot{r} + \Lambda \dot{e}) + C(\theta, \dot{\theta})(\dot{\theta}_r - r + \Lambda e) + F(\dot{\theta}) + G(\theta) + \tau_d = \tau + \tau_h$$

or more concisely as $$H(\theta)\dot{r} + C(\theta, \dot{\theta})r + \psi(x) + \tau_d = \tau + \tau_h \quad (8)$$

where x=[eT ėT θrT θ̇rT θ̈rT], and ψ is a nonlinear function that depends on the robot's uncertain parameters, defined as below.

$$\psi(x) = H(\theta)(\ddot{\theta}_r + \Lambda \dot{e}) + C(\theta, \dot{\theta})(\dot{\theta}_r + \Lambda e) + F(\dot{\theta}) + G(\theta) \quad (9)$$

As can be seen in (9), ψ is not a function of the prescribed admittance model parameters defined in (3), i.e., Mi and Di,i∈{x,y,ω}, which is different from typical admittance control schemes that rely on a model-following error as their trajectory-following objective [25].

The adaptive control scheme used in this study works based on an approximator that online-estimates the nonlinear ψ function given in (9) using a two-layer NN [26] as $$\psi(x) = W^T \sigma(V^T x) + \varepsilon \quad (10)$$

where W and V are the ideal weights, σ is the activation function vector, and ε is the approximation error of the NN approximator. If the approximated function is denoted by ψ̂, a control law can be formulated as $$\tau = \hat{\psi} + K_v r - v(t) \quad (11)$$

where $k_v > 0$ is a diagonal design parameter matrix, and v(t) is a term added for robustification against inaccuracies, variabilities, and unstructured disturbances in the robot's model. If we define Z as $$Z = \begin{bmatrix} \hat{W} & 0 \\ 0 & \hat{V} \end{bmatrix} \quad (12)$$

where Ŵ and V̂ are the approximate NN weights, the signal v(t) can be defined as $$v(t) = -K_z(Z_B + \|\hat{Z}\|_F)r \quad (13)$$

where Kz>0 is a scalar gain, $\|\cdot\|_F$ is the Frobenius norm operator, and $Z_B$ is a constant positive scalar bound on the NN weights such that $\|Z\|_F \leq Z_B$.

Incorporating (11) in (8) yields the sliding-mode error dynamics as $$H(\theta)\dot{r} + C(\theta, \dot{\theta})r + k_v r = \varepsilon + v + \tau_d \quad (14)$$

In practice, the ideal NN weights, W and V, are not known a priori, hence the following tuning algorithms are used in this study to compute and update Ŵ and V̂ online.

$$\dot{\hat{W}} = A\hat{\sigma}r^\tau - A\hat{\sigma}'\hat{V}^\tau xr^\tau - \kappa A\|r\|\hat{W} \quad (15)$$

$$\dot{\hat{V}} = Bx(\hat{\sigma}'^\tau \hat{W}r')^\tau - \kappa B\|r\|\hat{V} \quad (16)$$

$$\hat{\sigma}' = \text{diag}\{\sigma(\hat{V}^\tau x)\}[1 - \text{diag}\{\sigma(\hat{V}^\tau x)\}] \quad (17)$$

In these update equations, A and B are two positive definite matrices, σ(.) is the sigmoid activation function, and κ>0 is a small design parameter. Based on a rigorous Lyapunov argument in [15], it has been formally proven that the error signal defined in (5) converges zero when (15)-(17) are used as the tuning algorithm for the NN approximator. For in-depth discussion on the learning performance and proof of stability, refer to [15, 22, 23].

IV. Simulation Environment

Figure 12:
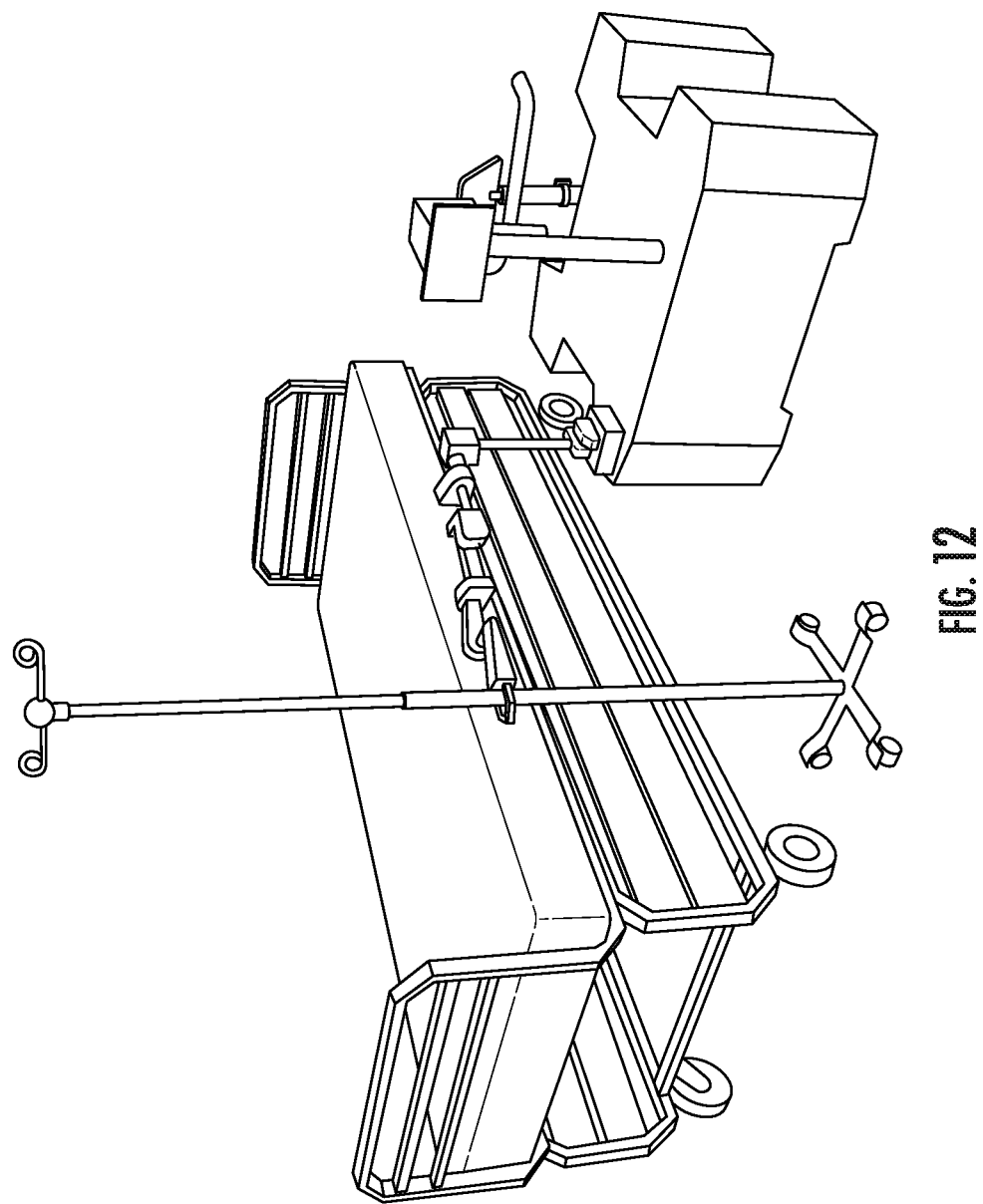
FIG. 12 shows a gazebo simulation environment including ARNA, hospital bed, and an IV pole.

In order to investigate its effectiveness, the proposed controller was implemented on a numerical model of ARNA in Gazebo simulator. Gazebo is an open-source software capable of dynamic simulation of sensors, robots, and their interaction with the environment based on multiple physics engines. In Gazebo, a robot and its environment are typically defined using a Unified Robot Description Format (URDF) file written in XML format. To develop the Gazebo model of ARNA, we first created ARNA's CAD model in Solid-Works® and utilized a plugin to convert it to a URDF format. In this model, the Mecanum wheels were simulated using Gazebo's planar move plugin. Another plugin was also developed that computes propulsion forces/torques exerted to the robot chassis by the wheels in each simulation step. Subsequently, in order to obtain realistic dynamic behavior of the model, we tuned its physical parameters including mass/inertia of different elements and joint viscous/coulomb frictions, as well as the friction between the Mecanum wheels and the ground. FIG. 12 depicts ARNA's model in Gazebo simulator.

To implement the admittance controller on the ARNA model, the Gazebo simulator was interfaced with Robot Operating System (ROS). ROS is a software framework for robot software development, and it provides services such as hardware abstraction, low-level device control, message-passing, and package management. In this study, Gazebo 8.6 with ODE physics engine and ROS Kinetic on Ubuntu 16.0 were used. Gazebo_ros_control plugin was utilized to facilitate communication between ROS packages by providing interfaces for robot joint actuation and robot data feedback. The Gazebo-ROS with the admittance controller was ran at 1 kHz.

V. Results and Discussion

For the sake of safety, velocity of the ARNA mobile platform is electronically limited to 0.4 m/s, 0.4 m/s, and 0.2 rad/s, in longitudinal, lateral, and rotational directions, respectively. Considering these limits, the virtual inertia and damping coefficients of the admittance model were defined. These numbers were chosen so that the robot can start and stop gently, and reach the aforementioned desired steady-state values in each respective direction, without excessive burden (forces and torque) required from a human user. For example, with 15 N force applied by the user in the longitudinal direction, the robot gently reaches the steady-state longitudinal velocity of 0.4 m/s in 2.5 s. The overall compliance behavior of the robot, however, depends on the bandwidth of both the prescribed admittance model and the neuroadaptive controller. Therefore, in this study, the parameters of the inner loop controller were tuned such that its bandwidth was at least twice that of the admittance model, and, hence, it could respond to the user input.

The presented admittance controller was implemented in our ROS-Gazebo simulation environment. The NN used had 2 layers, 21 inputs including bias, sigmoid activation functions, 15 neurons in the hidden layer, 4 outputs, and the weight matrices initialized with small random entries.

The simulations included two category of experiments to examine the efficacy of the proposed admittance controller and its inner-loop neuroadaptive controller. The first category of simulations were conducted considering only the nominal plant (i.e., robot without any payload). This category simply simulates a patient walking exercise in which a user applies forces and torques to the handlebar. In the second category of experiments, the robot pushed a 250-kg hospital bed fastened to the robot's frontal panel.

Figure 13:
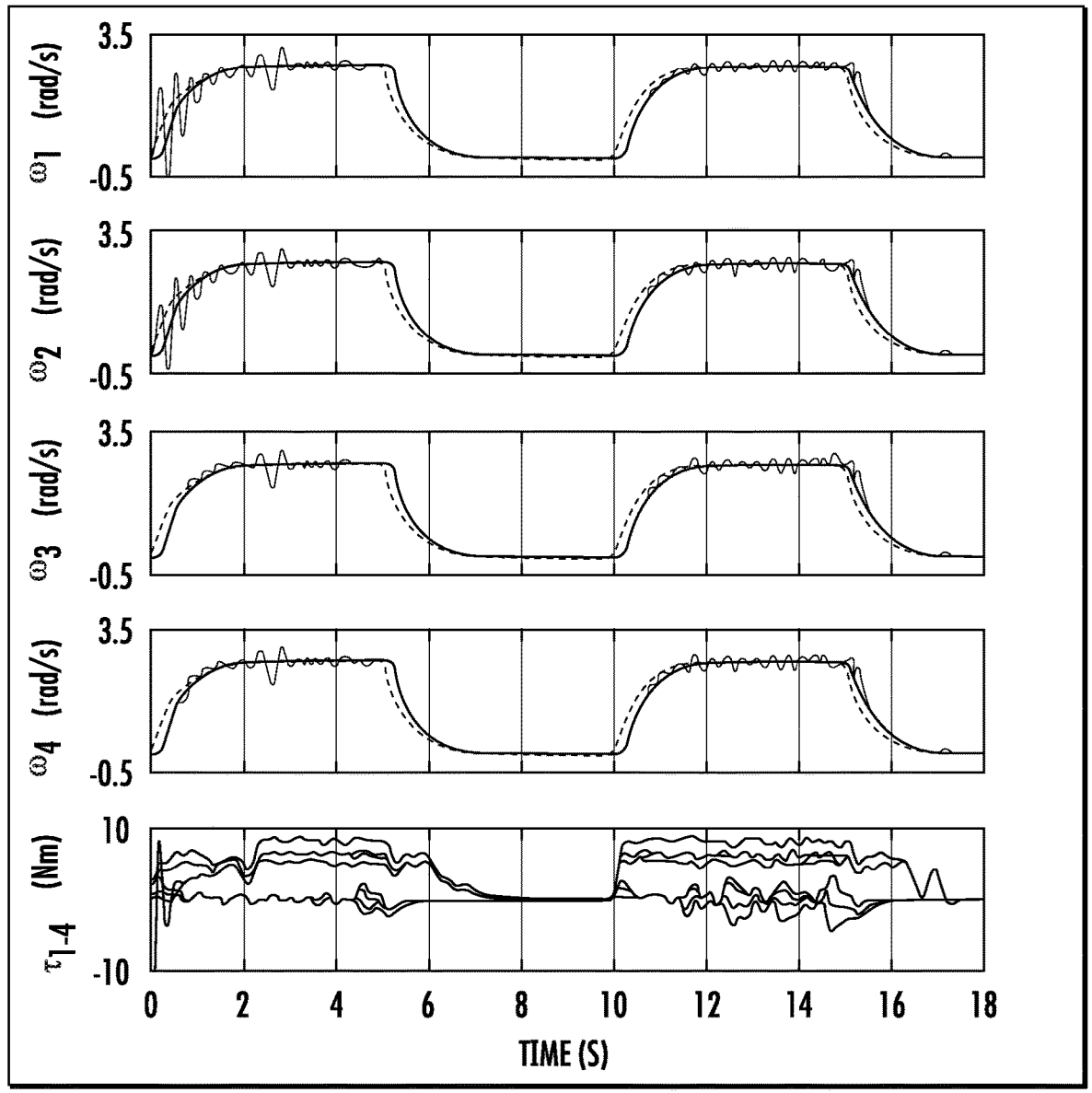
FIG. 13 shows individual joint velocities and control torque in response to force applied to the handlebar in longitudinal direction, i.e., fx=N. The dashed line is the output of admittance model for each joint. The blue trajectories are for the no-payload condition, and the red trajectories are for the with-payload condition.
Figure 14:
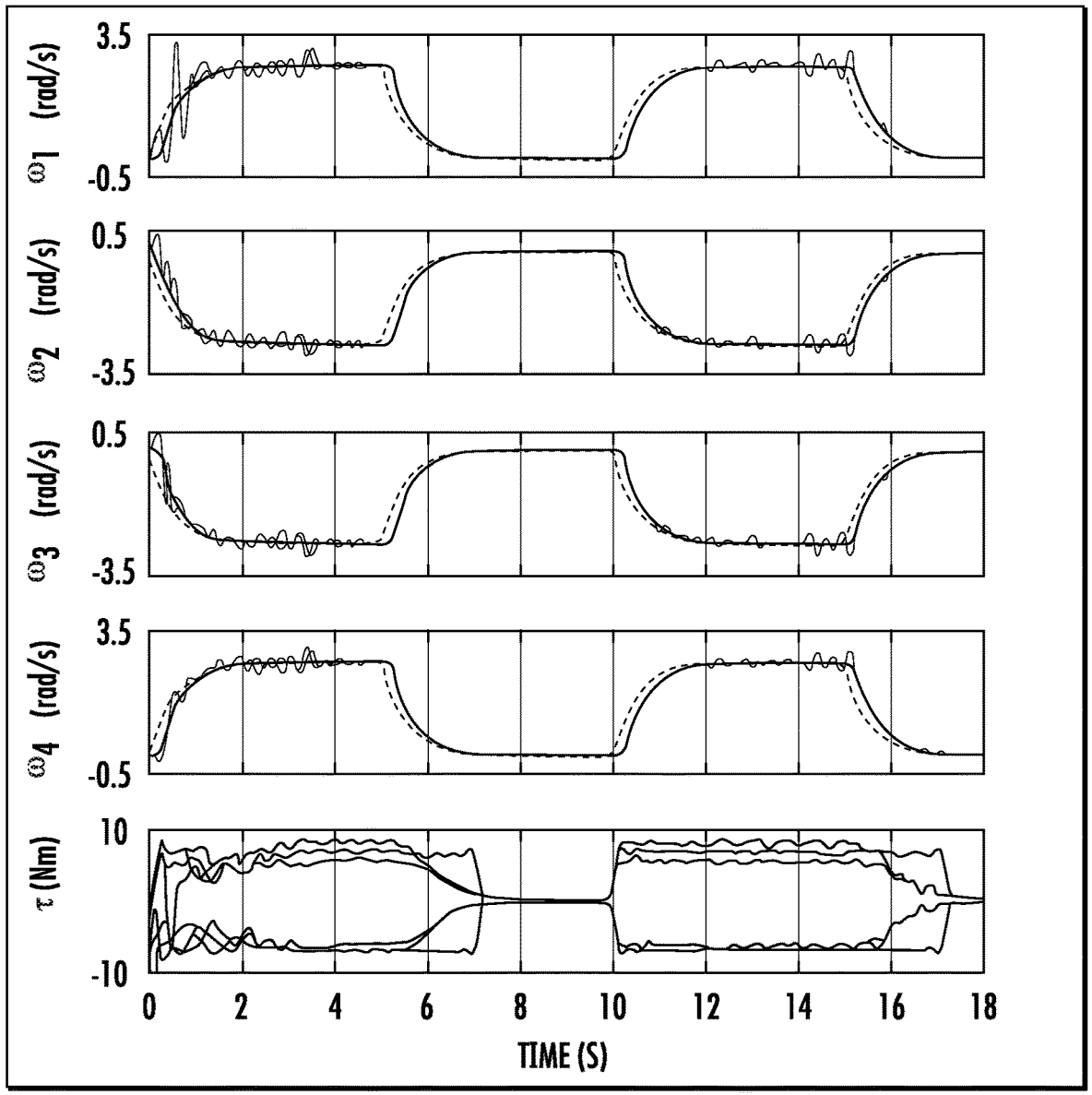
FIG. 14 shows individual joint velocities and control torque in response to force applied to the handlebar in lateral direction, i.e., fy=10 N. The dashed line is the output of admittance model for each joint. The blue trajectories are for the no-payload condition, and the red trajectories are for the with-payload condition.
Figure 15:
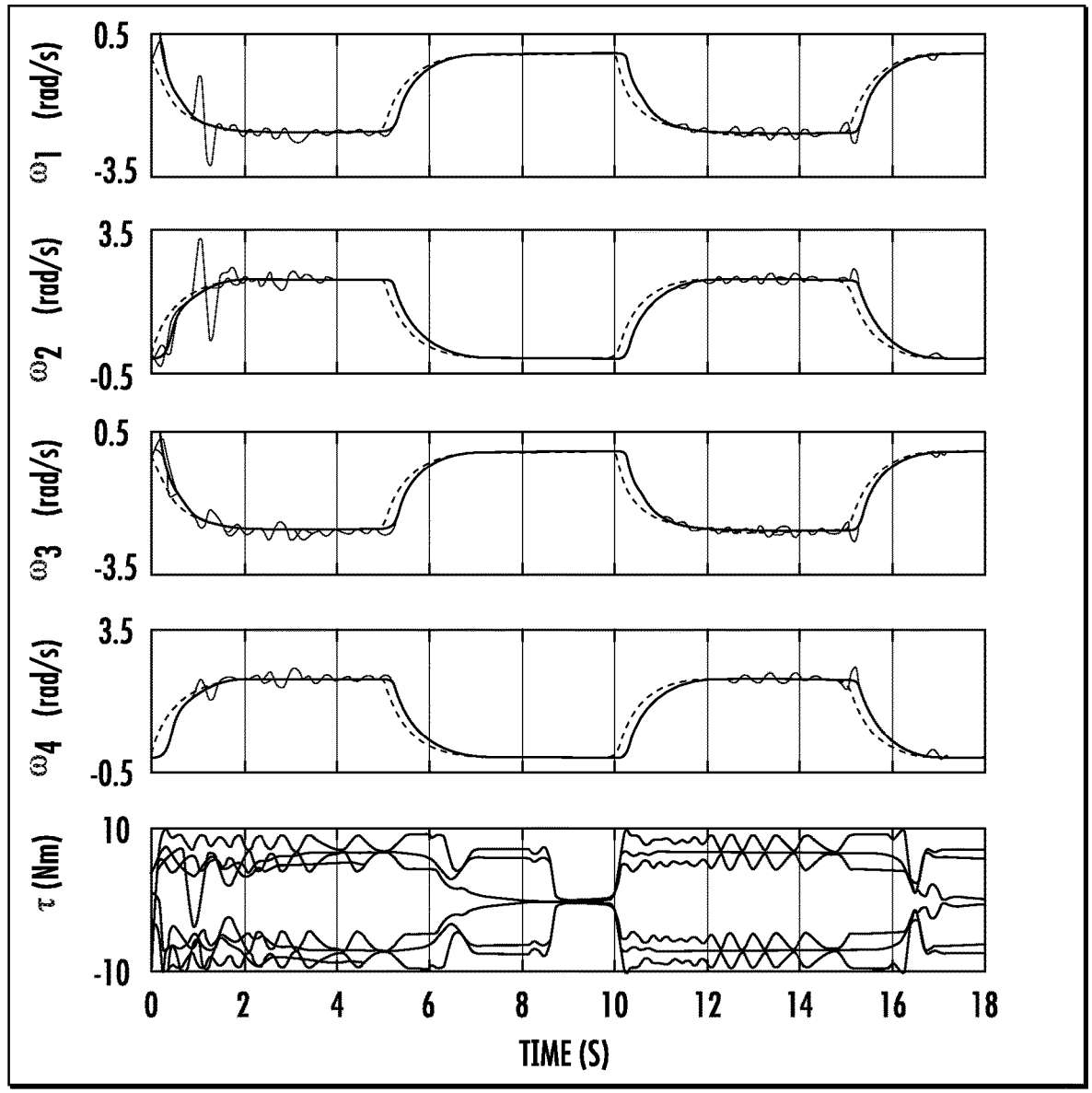
FIG. 15 shows individual joint velocities and control torque in response to torque applied to the handlebar in rotational direction, i.e., τz=4 Nm. The dashed line is the output of admittance model for each joint. The blue trajectories are for the no-payload condition, and the red trajectories are for the with-payload condition.
Figure 19:
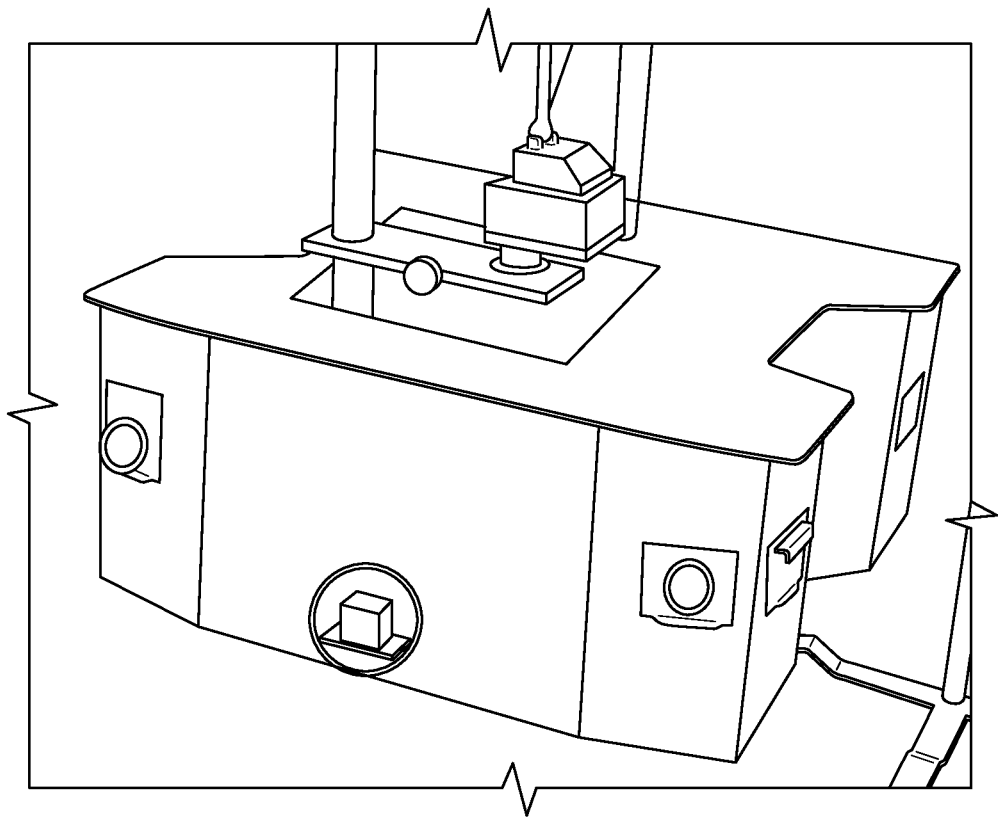
FIG. 19 is an image of the ARNA mobile robot, with the locations of the two front-side sensor blocks and the LIDAR highlighted.

For each category of experiments, three scenarios were simulated including independent force/torque commands, i.e., (a) fx=10 N, fy=0, τz=0, (b) fx=0, fy=10 N, τz=0, and (c) fx=0, fy=0, τz=4 Nm. In all scenarios, the robot were commanded to move starting from a standstill condition. FIGS. 13-15 illustrate the corresponding results including reference velocities in Cartesian space, reference and actual angles and velocities in joint space, and the required torques for each actuator.

VI. Conclusion

We introduced the Adaptive Robotic Nursing Assistant, designed to assist nurses with some of their physically-demanding tasks. ARNA has several human-machine interfaces, such as a custom-built tablet interface as well as a handlebar instrumented with a 6-axis force/torque sensor. We investigate the characteristics of the physical HRI between users and the ARNA through its handlebar that is enhanced by a NNs-based admittance controller which offers guaranteed stability and convergence. This admittance controller is designed in two decoupled steps; (i) a feed-forward admittance model that prescribes the compliant behavior of the robot in response to human efforts, and (ii) a neuroadaptive inner-loop controller that learns and compensates the nonlinearities and un-modelled dynamics of the robot online. Through extensive ROS-Gazebo simulations, we verify the effectiveness of the admittance controller in reducing sensitivity to the robot nonlinearities and inaccuracies, as well as the perturbations caused by substantial variation in payload condition.

REFERENCES

[1] Available: https://www.bls.gov/ooh/most-new-jobs.htm
[2] M. Kangasniemi, S. Karki, N. Colley, and A. Voutilainen, "The use of robots and other automated devices in nurses' work: An integrative review," *International journal of nursing practice*, p. e12739, 2019.
[3] J. Hu et al., "An advanced medical robotic system augmenting healthcare capabilities-robotic nursing assistant," in 2011 *IEEE international conference on robotics and automation*, 2011, pp. 6264-6269: IEEE.
[4] J. Li, Z. Li, and K. Hauser, "A study of bidirectionally telepresent tele-action during robot-mediated handover," in 2017 *IEEE International Conference on Robotics and Automation (ICRA)*, 2017, pp. 2890-2896: IEEE.
[5] Y. Liu, G. Chen, J. Liu, S. Guo, and T. Mukai, "Biomimetic Design of a Chest Carrying Nursing-Care Robot for Transfer Task," in 2018 *IEEE International Conference on Robotics and Biomimetics (ROBIO)*, 2018, pp. 45-50: IEEE.
[6] Z. Erickson, M. Collier, A. Kapusta, and C. C. Kemp, "Tracking human pose during robot-assisted dressing using single-axis capacitive proximity sensing," *IEEE Robotics and Automation Letters*, vol. 3, no. 3, pp. 2245-2252, 2018.
[7] A. Calanca, R. Muradore, and P. Fiorini, "A review of algorithms for compliant control of stiff and fixed-compliance robots," *IEEE/ASME Transactions on Mechatronics*, vol. 21, no. 2, pp. 613-624, 2015.
[8] N. Hogan, "Impedance control: An approach to manipulation," in 1984 *American control conference*, 1984, pp. 304-313: IEEE.
[9] R. J. Anderson and M. W. Spong, "Hybrid impedance control of robotic manipulators," *IEEE Journal on Robotics and Automation*, vol. 4, no. 5, pp. 549-556, 1988.
[10] T. Tsuji and Y. Tanaka, "Tracking control properties of human-robotic systems based on impedance control," *IEEE Transactions on systems, man, and cybernetics—Part A: Systems and Humans*, vol. 35, no. 4, pp. 523-535, 2005.
[11] C. L. Clover, G. R. Luecke, J. J. Troy, and W. A. McNeely, "Dynamic simulation of virtual mechanisms with haptic feedback using industrial robotics equipment," in *Proceedings of International Conference on Robotics and Automation*, 1997, vol. 1, pp. 724-730: IEEE.
[12] V. Duchaine and C. Gosselin, "Safe, stable and intuitive control for physical human-robot interaction," in 2009 *IEEE International Conference on Robotics and Automation*, 2009, pp. 3383-3388: IEEE.
[13] H. Kazerooni, T. Sheridan, and P. Houpt, "Robust compliant motion for manipulators, part I: The fundamental concepts of compliant motion," *IEEE Journal on Robotics and Automation*, vol. 2, no. 2, pp. 83-92, 1986.
[14] F. L. Lewis, D. M. Dawson, and C. T. Abdallah, *Robot manipulator control: theory and practice*. CRC Press, 2003.
[15] F. Lewis, S. Jagannathan, and A. Yesildirak, *Neural network control of robot manipulators and non-linear systems*. CRC Press, 1998.
[16] G. M. Atmeh, I. Ranatunga, D. O. Popa, K. Subbarao, F. Lewis, and P. Rowe, "Implementation of an adaptive, model free, learning controller on the Atlas robot," in 2014 *American Control Conference*, 2014, pp. 2887-2892: IEEE.
[17] I. Ranatunga, F. L. Lewis, D. O. Popa, and S. M. Tousif, "Adaptive admittance control for human-robot interaction using model reference design and adaptive inverse filtering," *IEEE Transactions on Control Systems Technology*, vol. 25, no. 1, pp. 278-285, 2016.
[18] Y. Wang, "Motion Performance Analysis and Layout Selection for Motion System with Four Mecanum Wheels," *Chinese Journal of Mechanical Engineering—CHIN J MECH ENG*, vol. 45, May 1, 2009.
[19] M. O. Tătar, C. Popovici, D. Mandru, I. Ardelean, and A. Pleşa, "Design and development of an autonomous omni-directional mobile robot with Mecanum wheels," in 2014 *IEEE International Conference on Automation, Quality and Testing, Robotics*, 2014, pp. 1-6: IEEE.
[20] W. S. Newman, "Stability and performance limits of interaction controllers," *Journal of dynamic systems, measurement, and control*, vol. 114, no. 4, pp. 563-570, 1992.
[21] K. S. Narendra and K. Parthasarathy, "Identification and control of dynamical systems using neural networks," *IEEE Transactions on neural networks*, vol. 1, no. 1, pp. 4-27, 1990.
[22] F. L. Lewis, K. Liu, and A. Yesildirek, "Neural net robot controller with guaranteed tracking performance," *IEEE Transactions on Neural Networks*, vol. 6, no. 3, pp. 703-715, 1995.
[23] F. L. Lewis, A. Yesildirek, and K. Liu, "Multilayer neural-net robot controller with guaranteed tracking performance," *IEEE Transactions on Neural Networks*, vol. 7, no. 2, pp. 388-399, 1996.
[24] M. M. Polycarpou, "Stable adaptive neural control scheme for nonlinear systems," *IEEE Transactions on Automatic control*, vol. 41, no. 3, pp. 447-451, 1996.

[25] E. Gribovskaya, A. Kheddar, and A. Billard, "Motion learning and adaptive impedance for robot control during physical interaction with humans," in 2011 *IEEE International Conference on Robotics and Automation*, 2011, pp. 4326-4332: IEEE.

[26] A. Yesildirek and F. L. Lewis, "Feedback linearization using neural networks," in *Proceedings of 1994 IEEE International Conference on Neural Networks (ICNN'94)*, 1994, vol. 4, pp. 2539-2544: IEEE.

ROSFuse: A High-Modularity ROS to Firmware Instrumentation Bridge for Robotic Sensors In this paper we present a modular software protocol for extending a variable dataspace within a microcontroller firmware system (MCU) that allows robotic sensor data to be streamed via the Robot Operating System (ROS) architecture. This protocol copies the data formatting structure inherent to ROS messages and implements a local Domain Name (DN) bridge to allow for asynchronous bi-directional data transport over any communication channel. We implement a demonstration of this system on a mobile robot test bed to manage communications between the sensor data acquisition MCU and the primary control computer, and use this test case to measure the efficacy of the protocol through latency and packet loss, and tracking validation by comparison to other measurement systems on the robot.

I. Introduction

In the course of development of large robotic systems, direct access to lower level hardware assets can rapidly become problematic [1]. Off-the shelf control hardware is rarely equipped to communicate with pin-level hardware [2]. Typically, CPU systems expect interaction to occur above the Hardware Abstraction Level (such as Ethernet, USB, Serial, and other related common communication protocols). Such interfaces can often be adapted to low-level sensors and actuators. Access to these assets on a CPU is typically in short supply compared to the span of instrumentation implemented on a robot [3]. For instance, one rarely finds more than 6-10 USB ports on a CPU, but this does not easily support sensor numbers in excess of a dozen. This issue could be approached by increasing port availability—by using USB hubs or Ethernet switches for instance—but this introduces problems as well. The reliability of port expansion, management of network systems, and the added bulk, complexity, and resource consumption are all potentially intractable on certain projects. Beyond these pragmatic concerns, there is also the effect on efficiency; complexity introduced from multiple communication hubs, added latency, and potentially significant computational overhead all limit performance. The natural and common response to these challenges is to implement low-level tasks with an appropriately low-level computation system and pass the resultant data to an interface for the CPU. This is where a CPU/MCU based system becomes most attractive, and where an efficient, scalable protocol for sharing data is essential. Robots have utilized this approach for decades, and there is a vast body of work associated with the equally vast number of options, which are most commonly specific to the application case. This is generally a matter of both expedience and pragmatism—a purpose-built design is typically the fastest and most reliable method of implementing communication between hardware systems [4]. However, the principle design issue these kinds of systems present is one of scalability [5]. When a system is designed optimally for a single use case, it is often the work of a complete re-design to expand it to accommodate changes.

In this paper, we are proposing a lightweight firmware-to-software bridge protocol which handles data transport between MCUs and CPUs. In particular, due to the ubiquity of ROS as a fundamental design tool for robotic software, we designed our system to integrate with, and mirror the structure of, ROS.

One method of achieving this same goal is via a hardware-based interface device. A widely adopted example of this is the National Instruments roboRIO. The roboRIO is a dedicated hardware platform carrying many embedded protocols and associated transport software. One such similar application to our demonstrator for ROSFuse is found in [6]. While highly efficient, this example also highlights common weaknesses of these hardware-focused interfaces. Though the roboRIO contains a wide range of interface, custom hardware is still required to bridge the gap between an atypical lowlevel sensor and the roboRIO. Other concerns include the cost-to-benefit ratio. With generalized hardware interfaces, there is often far more systematic and cost overhead present than is appropriate for an application case. When a dedicated microcontroller and a small amount of support hardware is more fitting, solutions like the roboRIO exhibit a low return on investment.

Alternative models have also been proposed which seek to remedy this problem, most notably architectures to manage communications across many devices. Below, we discuss several of these and discuss how our approach compares.

In [7], H-ROS, an architecture was developed towards achieving a ROS-compatible hardware standard. The architecture builds on ROS and has software features that facilitate access to the robot hardware and compartmentalization of software in different modes. Interoperability, reusability and reconfigurability are presented as the main benefits. However, because it is targeted for industrial use, it is built with features that limit wider adoption. One such facet is the EtherCAT Protocol used in the physical layer, which presents a whole level of integration beyond the base system being used.

A driver to interface Arduino-based robots with ROS is presented in [8]. Simulation and real-world navigation tasks are used to show functionality of the driver. While demonstrated to work well with different Arduino microcontrollers, scalability is shown only by adding only three singlevalue-output sensors to its test robot. Further, significant programming is required to integrate these sensors to ROS via the driver, as is typical of such bespoke systems.

By way of contrast, we also consider [9], in which the integration with ROS, is approached with a hardware-level firmware solution, implemented as a unified system on an FPGA. While this provides exceptional performance, the usage of single system chips is highly limiting with regards to modularity.

A similar approach to our concept has also been applied to the specific topic of sensor fusion in [10]. Herein the authors leverage the natural modular nature of ROS nodes to produce a generalized sensor fusion package which can be interfaced with other ROS ecosystem members. As with our methodology, the use of systematic design—relying on the publisher/subscriber paradigm—allows for the generation of scalable systems through ROS.

Our protocol was designed to possess following advantages over other frameworks including:

Scalability: Our protocol demonstrates strict linear relations between packet length and delay, and provides a mechanism for adding devices by editing only a configuration file.

Simplicity: our structure is designed specifically to copy the ROS ethos of configuration, allowing changes to variables to be made entirely independent of the source code Efficiency: we have made use of the ROS publisher/subscriber model for datasharing through message types. This allows us to implement variable sharing with minimal latency (187 uS).

We illustrate the advantages of ROSFuse in an application sensorizing a mobile manipulator robot in our lab. The robot included 32 sensors, whose data is streamed to a central CPU during environmental mapping and navigation. Results show that sensorization using the ROSFuse system enables high-speed transmission with a large number of sensors.

II. Protocol Description

In this section, we detail the design of the ROSFuse communication protocol. ROSFuse is structured to topically mimic ROS's publisher/subscriber framework, including the use of message definition files to define data types. The primary goal of the data share bridge is to make available in the ROS namespace variables which are set within the MCU, and vice-versa.

At the top level, this is achieved by a pair of processes: a ROS node running on the CPU, and an interrupt-driven process on the MCU. The ROS node retains a list of the topics initialized for data sharing, and the MCU process transfers data to and from variables internally. The ROS node subscribes to topics shared with the MCU and publishes topics shared from it, while the firmware interrupt routine parses data into variables, and transmits shared variables. This full workflow is illustrated in FIG. 3, and the procedure for message parsing in Algorithm 1.

---

Algorithm 1

---

```
procedure ROSFUSE_PARSE((Controls,Peripherals,Port))
  if Port.available( ) then
    while Port.next( ) ≠ "&" do Port.read( )
    packet ← ""
    while packet[−1] ≠ EOL do
      packet ← packet + Port.read( )
    Message ← packet.split(",")
    for ∀peripheral ∈ Peripherals do
      if peripheral.label == Message[0] then
        Current ← peripheral
    for datum ∈ peripheral do
      if datum.type[a] == Float then
        floatMember[a] = Message[a]
      if datum.type[a] == String then
        stringMembers[a] = Message[a]
      if datum.type[a] == Int then
        intMembers[a] = Message[a]
  for control ∈ Controls do
    packet ← "&"
    for datum ∈ control do packet ← packet + String(datum)
    packet ← "EOL"
    Port.write(packet)
```

---

A. Packet Structure

In order to implement any communication protocol, we must first select a packet type for the transmission itself. We select a simple string-based, delimited structure, as indicated in FIG. 16.

The advantages of using this format are three-fold:

I. Use of a string format simplifies parsing—though a numerical formatting system would enable for lower-overhead communication, the use of message namespace conventions when coupling to ROS dramatically simplifies the process of integration.

II. Messages formatted with start and end characters via the native string type can be of functionally unbounded length III. The use of the String type obviates the need for a complex encoding protocol for carrying strings—because packets are patched directly into a ROS topic, matching packet names to topics is both convenient for readability and identification.

As a further note, because the use of message type descriptors is copied from ROS to the firmware, there need not be any data included within the messages themselves to guide type selection, reducing packet size.

B. Message Definitions

In keeping with the design goal of matching the operational characteristics of the data bridge to ROS, we define two generic ROS message types to correspond to transmitted data. Each message type contains variable length arrays to store data, illustrated in FIG. 17.

On initialization of the ROS bridge node, the configuration file describing the message is read, generating instances of these topics. This configuration file serves to replace a concrete message definition for each data packet, enabling broad scalability. Further, the parameters for the hardware communication layer are within this configuration file.

Each message contains three primary fields—arrays for containing floating point, string, and integer data. In both the ROS and firmware packages, the data type field determines which array a specific datum is stored in. For instance, if the 4th member of a packet is an integer, then it will be stored in the 4th element of the integer member array, This indexing structure lets the MCU side system store any data type within a single object.

C. MCU Firmware

The primary component of the firmware side of the bridge is a C package, which defines the object handlers for both types of message, as well as a utility function for the transmission layer.

Within this package, there is an allocation for master lists of controls and peripherals. For controls, this list provides access to the variable list associated with the transmission, and for the peripherals the list of transmissions to be made. Objects for each message are created within the main execution loop and populate the list at time of creation.

Each peripheral initializer takes as input the transmission channel, name of the packet, number and type of data members associated with the transmission. The constructor for controls follows the same profile, where the process of variable insertion is handled upon receipt of a serial packet. Within the serial parser, a packet label is searched in the list of packet names for the associated control object, and data is placed into the object's corresponding data arrays.

The transmission read function required as input only a pointer to the object handler, and therefor is suitable for use within interrupt routines.

D. CPU Software

For the ROS implementation the task of reading, parsing, and writing to the transmission is augmented by the additional task of building and maintaining the ROS topic space. The ROS node package defines object types for the peripherals and controls, and packet parsing and variable storage components are exact parallels of the used in the MCU, just as the message structure and corresponding objects are analogous.

Figure 4:
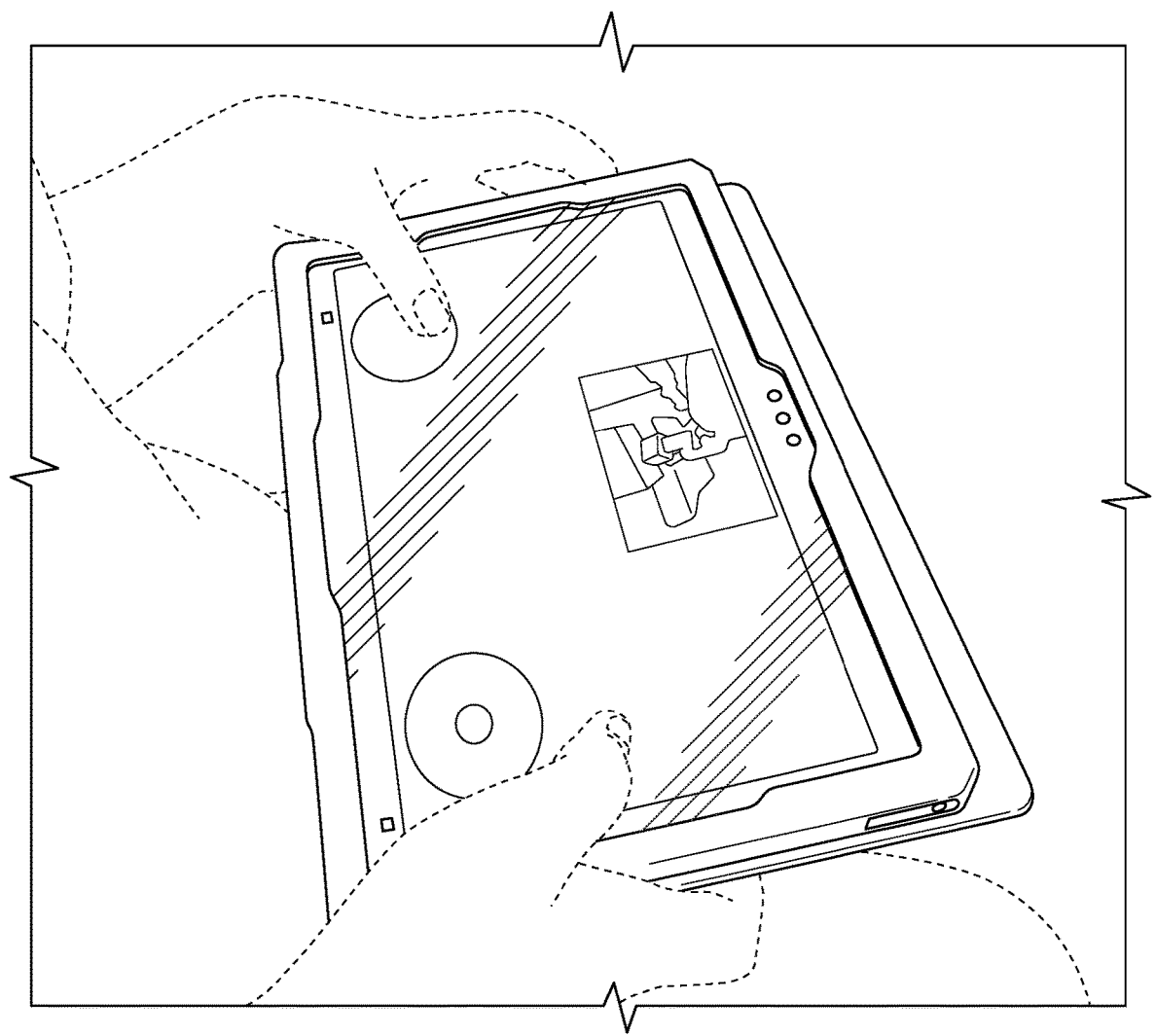
FIG. 4 shows a user using tablet interface showing camera feedback, and divot controls for base and arm teleoperation.

The ROS component begins with the configuration file, an example of which is illustrated in FIG. 4. This file defines the ROS topics and subscribers. It begins a subscriber topic for each control, and a publisher for each peripheral. The primary operation loop of the script alternately reads the transmission queue, collects peripheral reports and publishes them into the ROS topic space.

By contrast, control topics for the MCU are attached to the corresponding subscribers. When one of these topics is published, the subscriber collates the data from the publication, formats it into the transmission format, and writes it to the transmission medium.

III. Implementation System

To experimentally evaluate the performance of the protocol, we apply the above defined software components to the instrumentation of low-level sensors on a robotic platform.

A. MCU Hardware

We have built a custom interface board based on the PJRC Teensy 3.6 Arduino-compatible microcontroller. This MCU was selected for its high clock rate and large amount of IO, which considerably simplifies the PCB design.

Several of the sensors communicate over multi-device protocols, with 32 total devices reporting a total of 56 measurements. In our application, the sensors are arranged in 4 blocks of 8 each, with the control outputs being routed through individual terminal lines on the board.

B. Transmission Medium

For this system, we are using the built-in USB/Serial connection for transmission. The Teensy USB/Serial adapter always communicates at the USB limit of 12 Mbit/s, but we enable the standard hardware serial as well, enabling alternate baud rates for testing the effect of transmission speed on queuing loads and data rates.

C. Sensors

The sensor set was chosen to implement navigational assistance, making for a particularly diverse set of sensors. This is useful for testing as it enables increasing the number of sensors, variation in the data types, and the proportion thereof. As mentioned, the sensors are arranged in four 'blocks'. Each block contains three ultrasonic distance sensors, two button based contact sensors, two IR distance sensors for cliff detection, and one 9-DOF IMU.

D. Testbed Validation

To validate the efficacy of ROSFuse in a working context, we implement it on the Adaptive Robot Nursing Assistant (ARNA) platform, performing a navigation task. On this robot (seen in FIG. 5), ultrasonic sensors are used for obstacle avoidance, and a LIDAR range scanner is used for autonomous navigation. In order to demonstrate that the protocol is working effectively, utilize the range of the LIDAR scan corresponding to the sensing region of ultrasonic sensors in the same area. We compare these measurements as a function of time—one collected via the protocol and one independent of it.

Figure 20:
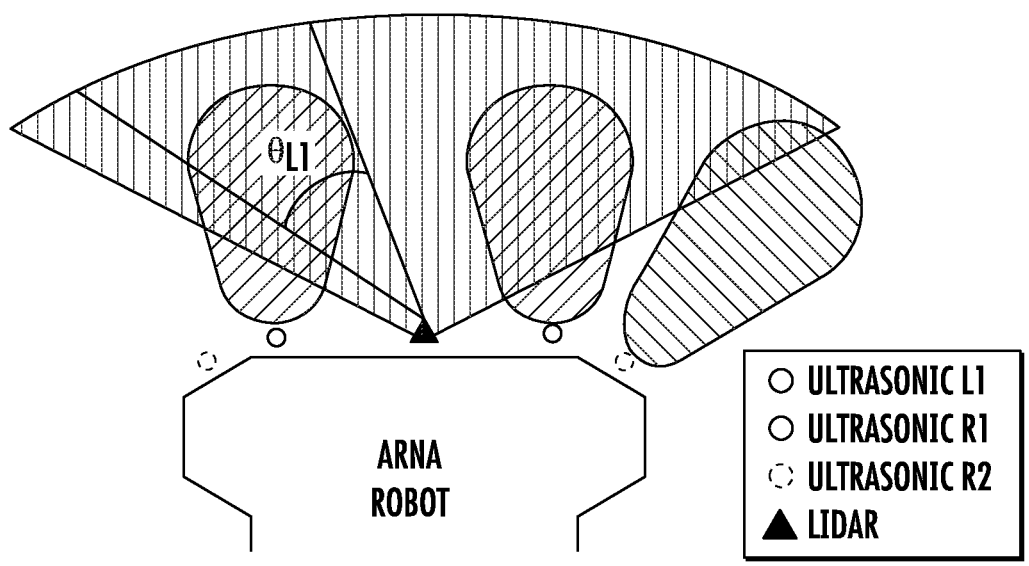
FIG. 20 is an illustration of the placement of the LIDAR and ultrasonic sensors, with relative sensing ranges shown (not to scale), and the corresponding angle in the scan range.

To properly correlate the regions, we collected both LIDAR and ultrasonic readings during a mapping exercise. Three of the 12 ultrasonic sensors on the robot share range with the LIDAR sensor, and within the LIDAR sweep, certain regions ($\theta_{L1}$, $\theta_{R1}$, $\theta_{R2}$,) correspond to their visibility range, as Illustrated in FIG. 20. We average the distance readings from the LIDAR scan across these areas.

Figure 21:
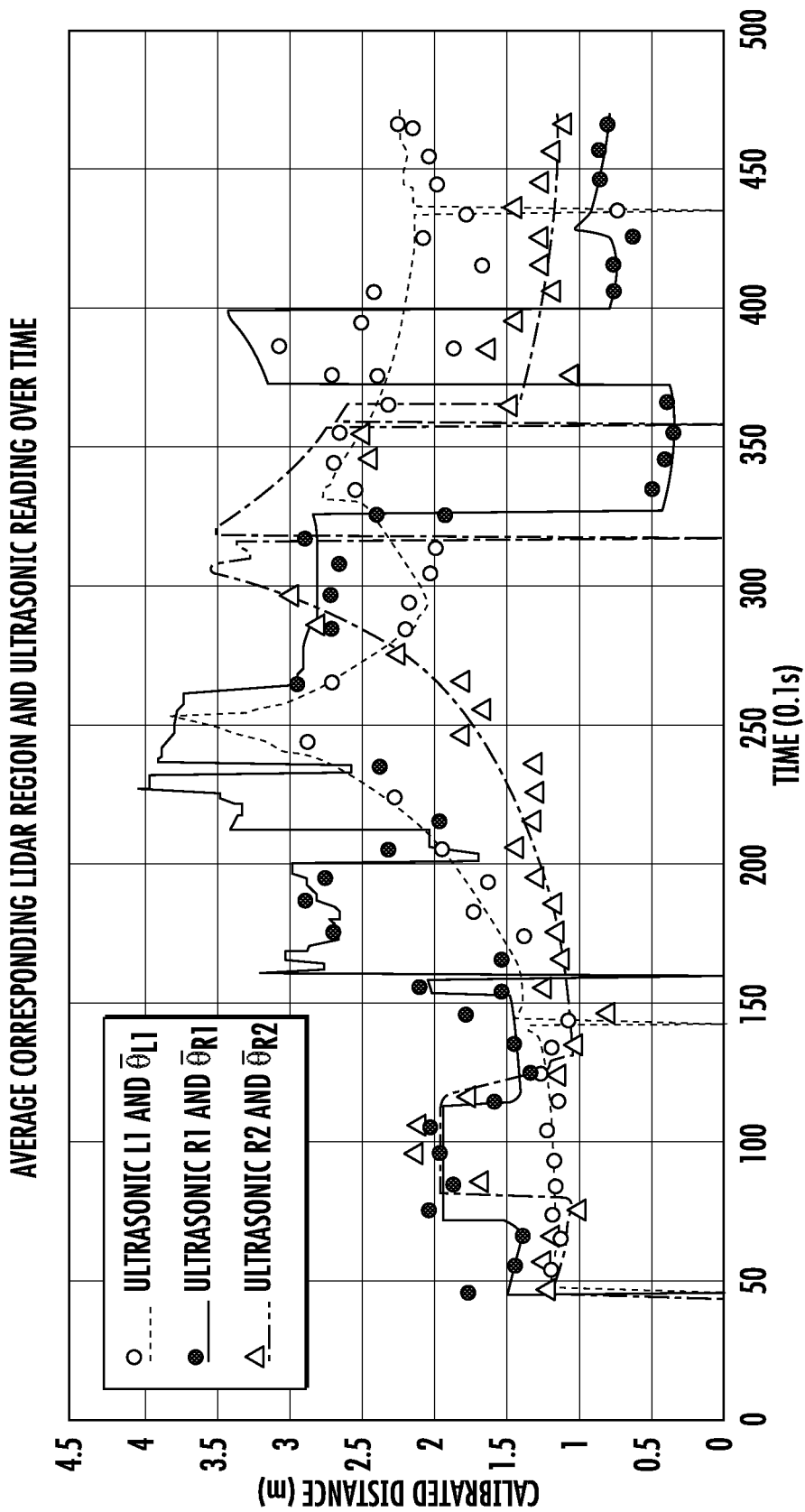
FIG. 21 is a plot of data from LIDAR corresponding region and Ultrasonic sensors mounted on the mobile robot as a function of step time (100 ms increments). In this figure, solid lines are the LIDAR readings, and single points are ultrasonic readings.
Figure 22:
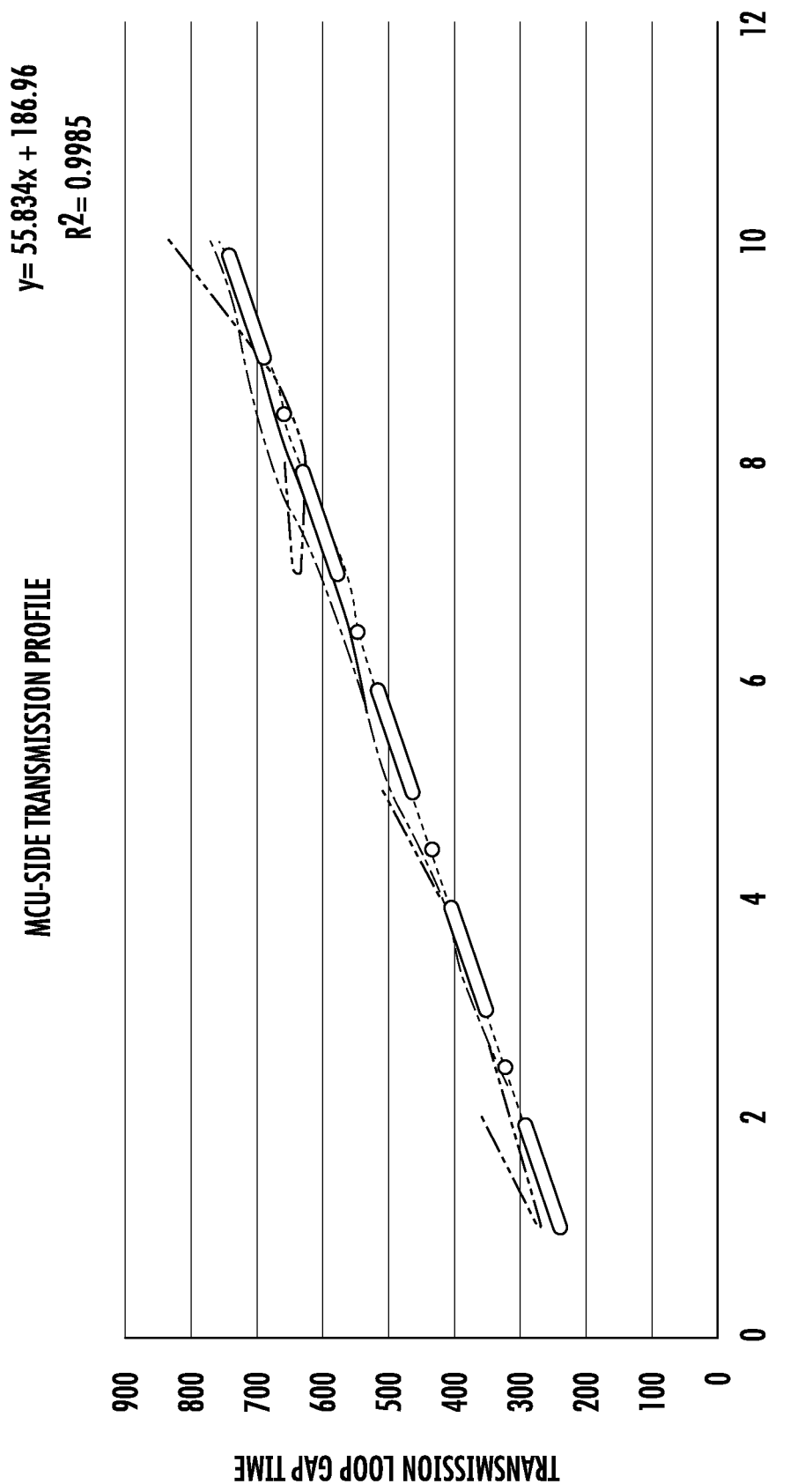
FIG. 22 shows a loading profile for the MCU side protocol, illustrating the linear profile, with the fit curve revealing the processing overhead limit of 187 μs and the per-datum rate of approximately 55 μs. Note that this is the upper bound of latency, not loop-back, timing.
Figure 23:
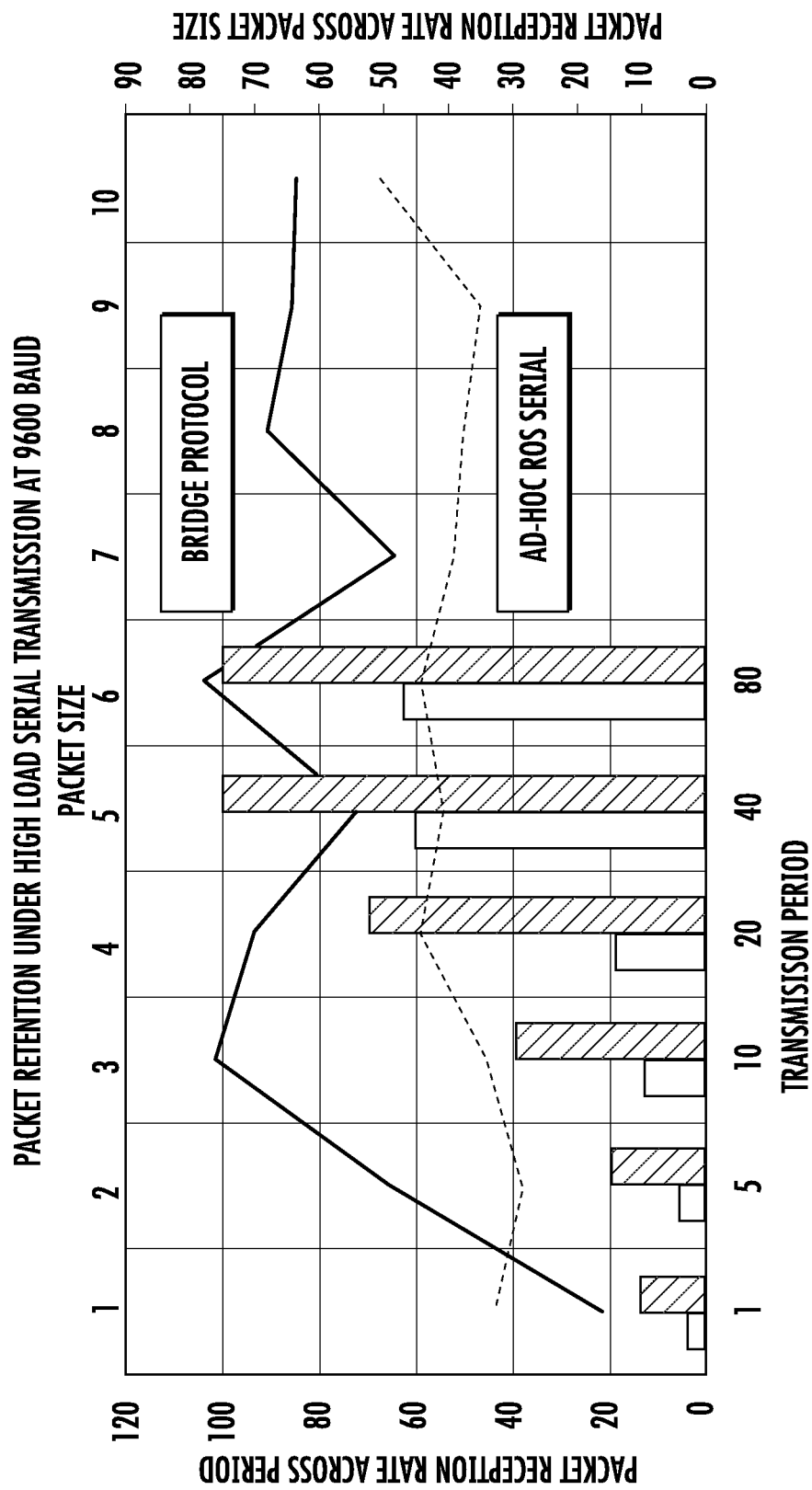
FIG. 23 is an illustration of packet transmission as a function of transmission period and average throughput over packet size, showing the functional inverse relationship between packet information density and transmission throughput, and comparing losses between the bridge protocol and brute-force ROS Serial.

The combined data set for these four sensors is plotted in FIG. 21, where the LIDAR data is divided into the three averaged regions corresponding to each ultrasonic sensor. On this graph, we can see that the Ultrasonic readings track well with the LIDAR data, staying at each time step within about a 15% margin of the LIDAR data, which is well within the measurement uncertainty of the ultrasonic sensors.

One notable observation is that there is no ultrasonic tracking periods of distances greater than approximately 3.2 m. This is due to hard-coded limits on the timing period of the ultrasonic sensor readings which limit their detection range to $2^7$ (128) inches.

IV. Data Collection & Analysis

In this section, we present diagnostic data illustrating the performance of the protocol under varying loads. In particular, we examine effectiveness using observations of these trends to predict behavior over a wider range of conditions.

A. Transmission Speed

Figure 8:
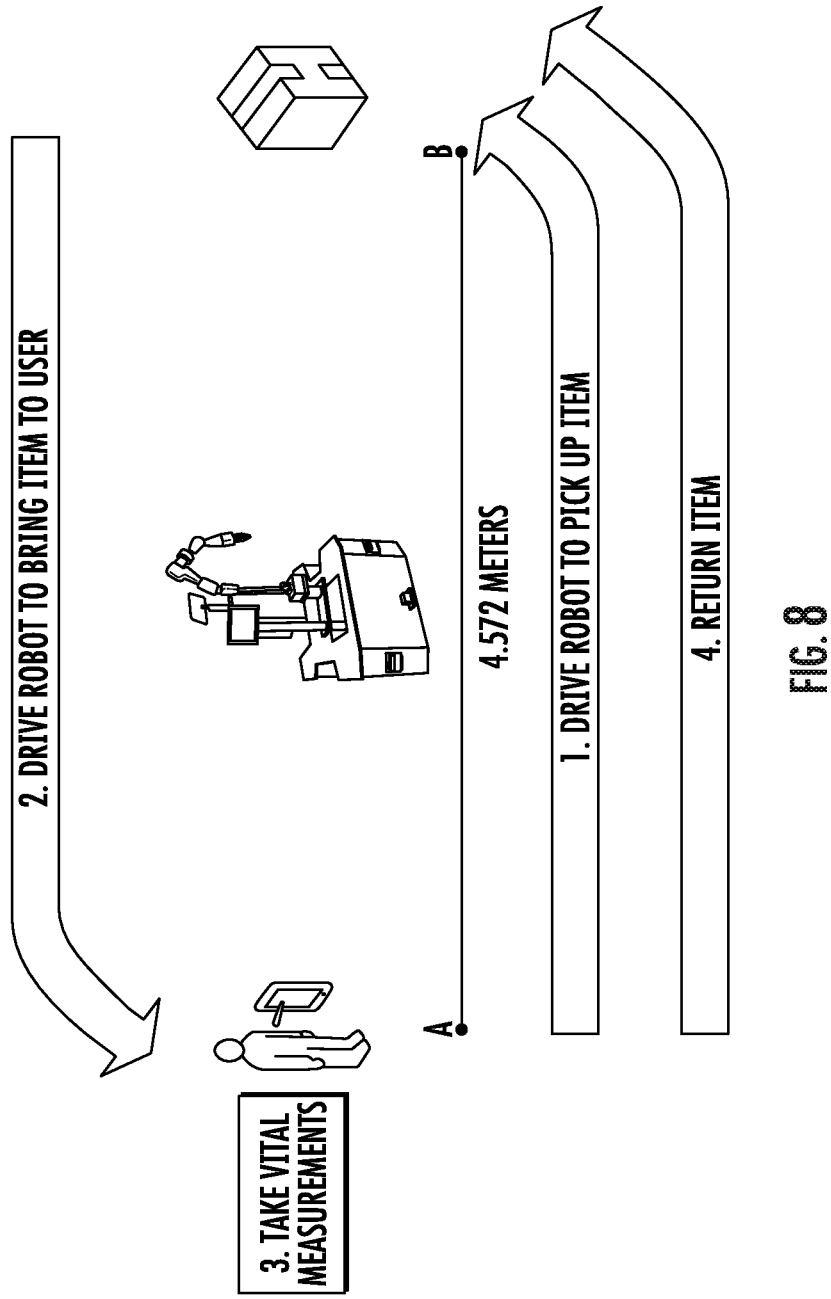
FIG. 8 illustrates an example patient sitter experiment.

To evaluate transmission speed, we implemented an interrupt-based timing check via the internal clock counter on the MCU, and the microsecond precision system clock on the CPU. For each of these assets, we collected interval period data across a range of transmission delays from 1 ms to 80 ms, and packet sizes from 1 to 10 random floating point numbers. FIG. 8 illustrates this averaged timing data. In this plot, we can observe the trending across both time- and data-density.

The first, and most important, observation we can make about these curves is that all are linear across both data density and period of transmission. This latter to 0.98. Further, each loading curve possesses an intercept within 3% of the average, indicating that the offset due to execution of ROSFuse is nearly constant with respect to packet size.

Second, the latency curves, illustrates that the overhead induced by ROSFuse is constant across period and load, fixed at 187 s. Further, the high correlation across different periods indicates a well-fit latency curve, as transmission lag does not vary with transmission period.

B. Packet Loss

To examine packet losses, we slow the transmission clock to 9600 baud, focusing on the MCU reception side. The CPU is easily able to outpace the MCU, even at maximal data rates. Conversely the CPU is capable of overwhelming the processing of the MCU at this lower transmission speed, with periods from 1 ms to 20 ms all bearing some degree of packet loss. The packet sizes at which loss occurs spans from nearly all at 1 ms to only intermittent losses at 20 ms. The data representing these losses is shown in FIG. 9, along with a parallel comparison to a direct data transmission via ROS Serial with no special handling, for comparison.

We also note that packet losses occurring at measurable rates have a consistent local peak loss around the middle of the data rate sweep. We interpret this as actual transmission time varying little between packet sizes and processing time generally being faster than transmission time, therefore, short packets are processed faster, but more frequently, while long packets have an effective transmission delay, allowing the MCU enough time to parse the data before the next packet finishes arriving.

Under these adversarial load conditions, we still receive a significant proportion of the transmitted data, with the average packet retention rate being around 13.7% for a single datum transmission at a 1 ms period. For a scope comparison, at 9600 baud, each character is allowed approximately 1.04 ms to transmit, meaning the 1 ms period consumes 96% of the available transmission time. By contrast, a direct transmission with bare ROS serial retains only 4% of packets under these conditions.

The critical factor underwriting this relatively low loss rate is the rapid packet checking. When a malformed packet Arrives at the bridge, it is discarded as soon as the error is detected, freeing buffer space. ROSFuse may then catch the next packet before buffer overflow occurs. Given that the latency overhead is known to be 187 s, the 1-datum latency 56 μs, and the transmission bound of 1040 μs, the available time for packet transmissions is $$\frac{1040\mu s - 187\mu s}{56\mu s},$$

fitting 15.5 transmissions per period. At the 96% consumption rate for 1 kHz transmissions, this yields a 14.9% upper bound for retention. Marginally more than our observed rate, but packet discard naturally cannot occur before some portion of the bandwidth is used reading the packet.

V. CONCLUSION

In this paper, we have presented and evaluated the performance of ROSFuse, a low-overhead, highly robust variable data-share system for integrating low-level hardware systems with ROS. We have described how this system offers benefits over other extant solutions to the problem of ROS integration by being more flexible and scalable than other software, lower overhead than framework models which seek to impose a design strategy, and sufficiently robust and efficient to outperform the native ROS protocols. Further, we illustrated the ease of implementation by utilizing the same definition file setup as ROS packages. This eliminated the need for source code changes to implement new hardware or modifications to old hardware. We also illustrated through experiments that the performance of the system remains effective under increasing loads. These experiments also demonstrated scalability, with the same hardware and software being used to test the 32 sensor board and the 10 reading performance experiment, observing high rate communication of 56 values with low latency (as tracked by the LIDAR comparison to the ultrasonic readings) directly into the ROS topic space.

In these experiments, we found that the performance is consistently linear over a range of loading and frequencies, and has a constant transmission latency. Our conclusion from this is that the protocol execution presents a nearly constant overhead and scales linearly with respect to the data size being transmitted.

Between the non-coding modular implementation for adding or changing data types, the paired bi-directional, medium-agnostic nature of the protocol, and the consistently low latency and linearity of speed over load, we believe that ROSFuse meets the standard of modular adaptability and scalability of ROS itself.

REFERENCES

[1] Ratasich, Denise, et al. Generic sensor fusion package for ROS. 2015 IEEE/RSJ International Conference on Intelligent Robots and Systems (IROS). IEEE, 2015.
[2] Groza, Voicu. Distributed framework for instrumentation hardware/software codesign. Proceedings of the 17th IEEE Instrumentation and Measurement Technology Conference [Cat. No. 00CH37066]. Vol. 3. IEEE, 2000.
[3] Arumugam, Rajesh, et al. DAvinCi: A cloud computing framework for service robots. 2010 IEEE international conference on robotics and automation. IEEE, 2010.
[4] Petersen, Robert, and Ron Harrison. Implementing a protocol abstraction layer architecture for interfacing heterogeneous software and hardware systems. IEEE Autotestcon, 2005. IEEE, 2005.
[5] Vuletic, Miljan, Laura Pozzi, and Paolo Ienne. Programming transparency and portable hardware interfacing: Towards general-purpose reconfigurable computing. Proceedings. 15th IEEE International Conference on Application-Specific Systems, Architectures and Processors, 2004. IEEE, 2004.
[6] Cremer, Sven, et al. Investigation of human-robot interface performance in household environments. Sensors for Next-Generation Robotics Ill. Vol. 9859. International Society for Optics and Photonics, 2016.
[7] Mayoral, Victor, et al. The shift in the robotics paradigm—The Hardware Robot Operating System (H-ROS); an infrastructure to create interoperable robot components. 2017 NASA/ESA Conference on Adaptive Hardware and Systems (AHS). IEEE, 2017.
[8] Ara'ujo, Andr'e, et al. Integrating Arduino-based educational mobile robots in ROS. Journal of Intelligent & Robotic Systems 77.2 (2015): 281-298.
[9] Steckhahn-Strohmer, Beck, et al. ROS-Enabled Hardware Framework for Experimental Robotics. International Conference on Reconfigurable Computing and FPGAs. 2019.
[10] Ratasich, Denise, et al. Generic sensor fusion package for ROS. 2015 IEEE/RSJ International Conference on Intelligent Robots and Systems (IROS). IEEE, 2015.

Various combinations and sub-combinations of the structures and features described in this specification are contemplated and will be apparent to a skilled person having knowledge of this disclosure. Any of the various features and elements as disclosed in this specification may be combined with one or more other disclosed features and elements unless indicated to the contrary.

Correspondingly, the subject matter as claimed is intended to be broadly construed and interpreted, as including all such variations, modifications and alternative embodiments, within its scope and including equivalents of the claims. It is understood that various details of the presently disclosed subject matter may be changed without departing from the scope of the claims. Furthermore, the foregoing description is for the purpose of illustration only, and not for the purpose of limitation.

What is claimed is:

1. An adaptive robotic nursing assistant comprising:
an omni-directional mobile platform;
a footrest on the omni-directional mobile platform;
a handlebar located above the footrest such that a user standing on the footrest can grasp the handlebar, wherein the handlebar comprises at least one sensor to measure a user interaction force;
a display above the handlebar and at least one user input device;
a robot manipulator comprising a robotic arm and an end-effector on the robotic arm; and
a control system coupled to the omni-directional mobile platform, the control system comprising at least one processor and memory storing executable instructions for the at least one processor to control the omni-directional mobile platform using the at least one sensor on the handlebar;
wherein the control system comprises a robot-specific neuroadaptive admittance controller for the omni-directional mobile platform, and wherein the control system is configured to use a feed-forward admittance model that generates a reference motion of the omni-directional mobile platform in response to the at least one sensor on the handlebar, so that the robot-specific neuroadaptive admittance controller tracks the reference motion of the omni-directional mobile platform.

2. The adaptive robotic nursing assistant of claim 1, wherein the omni-directional mobile platform comprises a base, a set of four wheels attached parallel to each other around a periphery of the base, and a set of four motors configured to individually drive each of the four wheels.

3. The adaptive robotic nursing assistant of claim 1, wherein the handlebar comprises electronic skin wrapped around at least one gripping portion of the handlebar, and wherein the electronic skin is coupled to the control system.

4. The adaptive robotic nursing assistant of claim 1, wherein the robotic arm comprises a six degree-of-freedom (DOF) robotic arm or a seven DOF robotic arm, and wherein the end-effector of the robotic arm comprises a gripper.

5. The adaptive robotic nursing assistant of claim 1, comprising one or more force/torque (FT) sensors coupled to the control system, wherein the control system is configured to execute a whole-body collision detection algorithm using sensor signals from the FT sensors.

6. The adaptive robotic nursing assistant of claim 1, comprising at least one force/torque (FT) sensor placed on the omni-directional mobile platform underneath an attachment point of the robot manipulator.

7. The adaptive robotic nursing assistant of claim 1, wherein the control system comprises at least two separate computer systems including a first computer system executing a real-time robot motion control algorithm and a second computing system processing sensor signals from a camera and one or more other sensors.

8. The adaptive robotic nursing assistant of claim 1, comprising a plurality of sensors distributed in sensor boxes located around a periphery of the omni-directional mobile platform, wherein the plurality of sensors includes at least one infrared (IR) sensor, at least one proximity sensor, and at least one bump sensor.

9. The adaptive robotic nursing assistant of claim 1, wherein the robot-specific adaptive admittance controller is configured to receive a sensor signal from at least one sensor on the handlebar and to output at least one control signal to the omni-directional mobile platform.

10. The adaptive robotic nursing assistant of claim 9, wherein the at least one sensor comprises a 6-axis force/torque sensor.

11. The adaptive robotic nursing assistant of claim 1, wherein the robot-specific adaptive admittance controller is configured to convert a reference motion of the omni-directional mobile platform to a separate wheel reference motion for each wheel of a plurality of wheels of the omni-directional mobile platform using inverse kinematics.

12. The adaptive robotic nursing assistant of claim 1, wherein the robot-specific adaptive admittance controller comprises a closed-loop neuroadaptive controller.

13. The adaptive robotic nursing assistant of claim 12, wherein the inner-loop neuroadaptive controller comprises a torque controller configured to emulate a mechanical system with one or more target admittance characteristics.

14. The adaptive robotic nursing assistant of claim 1, wherein a mechanical adapter mechanism allows the end-effector to hold UV light source or disinfectant liquid sprayer mechanism.

15. The adaptive robotic nursing assistant of claim 14, wherein the robot arm is configured to operate alongside an autonomous navigation algorithm to navigate facilities and perform sanitization activity on commonly touched surfaces which include but not restricted to doorknobs, tabletops, door-handle, hospital beds and walls.

16. The adaptive robotic nursing assistant of claim 14, wherein the robotic arm is controlled to hover over surfaces to either spray disinfectants or expose them to UV-C light for disinfection.

17. The adaptive robotic nursing assistant of claim 1, comprising a riser mechanism to increase/decrease the operating height of the platform on which the robot manipulator is installed.

18. The adaptive robotic nursing assistant of claim 1, comprising a display unit at the front of the robot to provide visual instructions and feedback during robot operation.

* * * * *